US011243213B2

(12) United States Patent
Tarca et al.

(10) Patent No.: US 11,243,213 B2
(45) Date of Patent: Feb. 8, 2022

(54) KITS AND METHODS FOR PREDICTION AND TREATMENT OF PREECLAMPSIA

(71) Applicants: WAYNE STATE UNIVERSITY, Detroit, MI (US); THE UNITED STATES OF AMERICA AS REPRESENTED BY THE SECRETARY, DEPARTMENT OF HEALTH AND HUMAN SERVICE, Bethesda, MD (US)

(72) Inventors: Adi L. Tarca, South Lyon, MI (US); Piya Chaemsaithong, Shatin (HK); Tinnakorn Chaiworapongsa, Grosse Pointe Park, MI (US); Sonia S. Hassan, Novi, MI (US); Roberto Romero, Grosse Pointe, MI (US)

(73) Assignees: Wayne State University, Detroit, MI (US); The United States of America as Represented by the Secretary, Department of Health and Human Services, Bethesda, MD (US)

(*) Notice: Subject to any disclaimer, the term of this patent is extended or adjusted under 35 U.S.C. 154(b) by 572 days.

(21) Appl. No.: 15/773,978

(22) PCT Filed: Nov. 7, 2016

(86) PCT No.: PCT/US2016/060825
§ 371 (c)(1),
(2) Date: May 4, 2018

(87) PCT Pub. No.: WO2017/079741
PCT Pub. Date: May 11, 2017

(65) Prior Publication Data
US 2018/0328937 A1    Nov. 15, 2018

Related U.S. Application Data

(60) Provisional application No. 62/251,589, filed on Nov. 5, 2015.

(51) Int. Cl.
*G01N 33/53* (2006.01)
*G01N 33/68* (2006.01)
*C12Q 1/6883* (2018.01)
*A61K 35/16* (2015.01)

(52) U.S. Cl.
CPC .......... *G01N 33/689* (2013.01); *A61K 35/16* (2013.01); *C12Q 1/6883* (2013.01); *C12Q 2600/158* (2013.01); *C12Y 304/24007* (2013.01); *G01N 2333/96494* (2013.01); *G01N 2800/52* (2013.01)

(58) Field of Classification Search
None
See application file for complete search history.

(56) References Cited

U.S. PATENT DOCUMENTS

| | | | | |
|---|---|---|---|---|
| 5,545,616 A | * | 8/1996 | Woodruff | A61K 38/1709 514/8.9 |
| 2005/0250156 A1 | * | 11/2005 | Shebuski | G01N 33/6893 435/7.1 |
| 2008/0267973 A1 | * | 10/2008 | Wang | A61P 1/16 424/153.1 |
| 2010/0267034 A1 | | 10/2010 | Lo et al. | |
| 2014/0141456 A1 | * | 5/2014 | Kumar | G01N 33/689 435/7.92 |
| 2014/0154691 A1 | * | 6/2014 | Chapman | G01N 33/57407 435/6.12 |
| 2014/0287947 A1 | * | 9/2014 | Boniface | G16B 20/00 506/9 |

FOREIGN PATENT DOCUMENTS

WO    WO2013188686    12/2013

OTHER PUBLICATIONS

Voller Alister, Diagnostic Horizons, Dynasciences Corportion, Published by Microbiological Associates, vol. 2, No. 1, Feb. 1978, pp. 1-7. (Year: 1978).*
Brou et al., Dysregulated biomarkers induce distinct pathways in preterm birth, BJOG An International Journal of Obstetrics and Gynaecology, 2012, pp. 458-473. (Year: 2012).*
Galewska et al., Matrix metalloproteinases, MMP-7 and MMP-26 in plasma and serum of control and preeclamptic umbilical cord blood, European Journal of Obstetrics & Gynecology and Reproductive Biology, 150 (2010), pp. 152-156. (Year: 2010).*
Gold et al., Aptamer-based multiplexed proteomic technology for biomarker discovery, Nature Precedings, Jun. 14, 2010. (Year: 2010).*
Gandemer et al., Pregnancy-associated autoimmune neonatal thrombocytopenia: role of maternal HLA genotype, British Journal of Haematology 1999, 104, pp. 878-885. (Year: 1999).*
Davies, et al., "Unique motifs and hydrophobic interactions shape the binding of modified DNA ligands to protein targets," PNAS USA, vol. 109, No. 49, 2012, pp. 19971-19976.
Gold, et al., "Aptamer-based multiplexed proteomic technology for biomarker discovery," PLoS One, vol. 5, No. 12, 2010, 17 pages.
Wu, et al., "Early Pregnancy Biomarkers in Pre-Eclampsia: A Systematic Review and Meta-Analysis," International Journal of Molecular Sciences, vol. 16, No. 9, 2015, pp. 23035-23056.
Eide, et al., "Decidual Expression and Maternal Serum Levels of Heme Oxygenase 1 are Increased in Pre-eclampsia," Acta Obstetricia et Gynecologica, vol. 87, No. 3, 2008, pp. 272-279.

(Continued)

*Primary Examiner* — Gary Counts
(74) *Attorney, Agent, or Firm* — Tanya M. Harding; Lee & Hayes, P.C.

(57) ABSTRACT

Biomarkers tests which can be used to predict a positive or negative risk of preeclampsia are described. More specifically, a panel of biomarkers including MMP-7 and gpIIbIIIa, described. The test is useful to predict preeclampsia when a biological sample is obtained between the 16th and 22nd week of pregnancy. Prediction later in pregnancy can be achieved by a combination of Siglec-6, Activin A, ALCAM, and/or FCN2.

12 Claims, 14 Drawing Sheets

Specification includes a Sequence Listing.

(56) References Cited

OTHER PUBLICATIONS

Oshaughnessy, et al., "Thrombophilic Polymorphisms in Pre-eclampsia: Altered Frequency of the Functional 98C>T Polymorphism of Glycoprotein IIIa," Journal of Medical Genetics, vol. 38, No. 11, 2001, pp. 775-777.
Podymow, et al., "Update on the Use of Antihypertensive Drugs in Pregnancy Hypertension," vol. 51, No. 4, 2008, pp. 960-969.
Przybl, et al., "CD74-Downregulation of Placental Macrophage-Trophoblastic Interactions in Preeclampsia," Circ. Res., vol. 119, No. 1, 2016, pp. 55-68.
Reister, et al., "Altered Protease Expression by Periarterial Trophoblast Cells in Severe Early-Onset Preeclampsia with IUGR," J. Perinat. Med., vol. 34, No. 4, 2006, pp. 272-279.
Seo, et al., "Regioselective Covalent Immobilization of Recombinant Antibody Binding Proteins A, G, and Protein L for Construction of Antibody Arrays" J. Am Chem. Soc., vol. 135, No. 24, 2013, pp. 1-19.
Search Report and Written Opinion dated Mar. 27, 2017 in International Patent Application No. PCT/US2016/060825.
Wang, et al., "Innate Immune Response by Ficolin Binding in Apoptotic Placenta Is Associated with the Clinical Syndrome of Preeclampsia," Clin. Chem., vol. 53, No. 1, 2007, pp. 42-52.

\* cited by examiner

FIG. 1

MRLTVLCAVCLLPGSLALPLPQEAGGMSELQWEQAQDYLKRFYLYDSETKNANSLEAK
LKEMQKFFGLPITGMLNSRVIEIMQKPRCGVPDVAEYSLFPNSPKWTSKVVTYRIVSYTR
DLPHITVDRLVSKALNMWGKEIPLHFRKVVWGTADIMIGFARGAHGDSYPFDGPGNTLA
HAFAPGTGLGGDAHFDEDERWTDGSSLGINFLYAATHELGHSLGMGHSSDPNAVMYP
TYGNGDPQNFKLSQDDIKGIQKLYGKRSNSRKK    (SEQ ID NO: 1)

FIG. 2A

MARALCPLQALWLLEWVLLLLGACAAPPAWALNLDPVQLTFYAGPNGSQFGFSLDFHK
DSHGRVAIVVGAPRTLGPSQEETGGVFLCPWRAEGGQCPSLLFDLRDETRNVGSQTLQ
TFKARQGLGASVVSWSDVIVACAPWQHWNVLEKTEEAEKTPVGSCFLAQPESGRRAEY
SPCRGNTLSRIYVENDFSWDKRYCEAGFSSVVTQAGELVLGAPGGYYFLGLLAQAPVA
DIFSSYRPGILLWHVSSQSLSFDSSNPEYFDGYWGYSVAVGEFDGDLNTTEYVVGAPT
WSWTLGAVEILDSYYQRLHRLRAEQMASYFGHSVAVTDVNGDGRHDLLVGAPLYMDSR
ADRKLAEVGRVYLFLQPRGPHALGAPSLLLTGTQLYGRFGSAIAPLGDLRDGYNDIAVA
APYGGPSGRGQVLVFLGQSEGLRSRPSQVLDSPFPTGSAFGFSLRGAVDIDDNGYPDLI
VGAYGANQVAVYRAQPVVKASVQLLVQDSLNPAVKSCVLPQTKTPVSCFNIQMCVGAT
GHNIPQKLSLNAELQLDRQKPRQGRRVLLLGSQQAGTTLDLDLGGKHSPICHTTMAFLR
DEADFRDKLSPIVLSLNVSLPPTEAGMAPAVVLHGDTHVQEQTRIVLDCGEDDVCVPQL
QLTASVTGSPLLVGADNVLELQMDAANEGEGAYEAELAVHLPQGAHYMRALSNVEGFE
RLICNQKKENETRVVLCELGNPMKKNAQIGIAMLVSVGNLEEAGESVSFQLQIRSKNSQN
PNSKIVLLDVPVRAEAQVELRGNSFPASLVVAAEEGEREQNSLDSWGPKVEHTYELHNN
GPGTVNGLHLSIHLPGQSQPSDLLYILDIQPQGGLQCFPQPPVNPLKVDWGLPIPSPSPI
HPAHHKRDRRQIFLPEPEQPSRLQDPVLVSCDSAPCTVVQCDLQEMARGQRAMVTVLA
FLWLPSLYQRPLDQFVLQSHAWFNVSSLPYAVPPLSLPRGEAQVWTQLLRALEERAIPI
WWVLVGVLGGLLLLTILVLAMWKVGFFKRNRHTLEEDDEEGE    (SEQ ID NO: 2)

FIG. 2B

MARALCPLQALWLLEWVLLLLGACAAPPAWALNLDPVQLTFYAGPNGSQFGFSLDFHK
DSHGRVAIVVGAPRTLGPSQEETGGVFLCPWRAEGGQCPSLLFDLRDETRNVGSQTLQ
TFKARQGLGASVVSWSDVIVACAPWQHWNVLEKTEEAEKTPVGSCFLAQPESGRRAEY
SPCRGNTLSRIYVENDFSWDKRYCEAGFSSVVTQAGELVLGAPGGYYFLGLLAQAPVA
DIFSSYRPGILLWHVSSQSLSFDSSNPEYFDGYWGYSVAVGEFDGDLNTTEYVVGAPT
WSWTLGAVEILDSYYQRLHRLRAEQMASYFGHSVAVTDVNGDGRHDLLVGAPLYMDSR
ADRKLAEVGRVYLFLQPRGPHALGAPSLLLTGTQLYGRFGSAIAPLGDLRDGYNDIAVA
APYGGPSGRGQVLVFLGQSEGLRSRPSQVLDSPFPTGSAFGFSLRGAVDIDDNGYPDLI
VGAYGANQVAVYRAQPVVKASVQLLVQDSLNPAVKSCVLPQTKTPVSCFNIQMCVGAT
GHNIPQKLSLNAELQLDRQKPRQGRRVLLLGSQQAGTTLDLDLGGKHSPICHTTMAFLR
DEADFRDKLSPIVLSLNVSLPPTEAGMAPAVVLHGDTHVQEQTRIVLDCGEDDVCVPQL
QLTASVTGSPLLVGADNVLELQMDAANEGEGAYEAELAVHLPQGAHYMRALSNVEGFE
RLICNQKKENETRVVLCELGNPMKKNAQIGIAMLVSVGNLEEAGESVSFQLQIRSKNSQN
PNSKIVLLDVPVRAEAQVELRGNSFPASLVVAAEEGEREQNSLDSWGPKVEHTYELHNN
GPGTVNGLHLSIHLPGQSQPSDLLYILDIQPQGGLQCFPQPPVNPLKVDWGLPIPSPSPI
HPAHHKRDRRQIFLPEPEQPSRLQDPVLVSCDSAPCTVVQCDLQEMARGQRAMVTVLA
FLWLPSLYQRPLDQFVLQSHAWFNVSSLPYAVPPLSLPRGEAQVWTQLLRALEERAIPI
WWVLVGVLGGLLLLTILVLAMWKVGFFKRNRHTLEEDDEEGE    (SEQ ID NO: 2)

FIG. 3

MLPLLLPLLWAGALAQERRFQLEGPESLTVQEGLCVLVPCRLPTTLPASYYGYGYWF
LEGADVPVATNDPDEEVQEETRGRFHLLWDPRRKNCSLSIRDARRRDNAAYFFRLKS
KWMKYGYTSSKLSVRVMALTHRPNISIPGTLESGHPSNLTCSVPWVCEQGTPPIFSW
MSAAPTSLGPRTTQSSVLTITPRPQDHSTNLTCQVTFPGAGVTMERTIQLNVSYAPQK
VAISIFQGNSAAFKILQNTSSLPVLEGQALRLLCDADGNPPAHLSWFQGFPALNATPIS
NTGVLELPQVGSAEEGDFTCRAQHPLGSLQISLSLFVHWSSAPVPDRHSFRPPC
(SEQ ID NO: 4)

FIG. 4

MPLLWLRGFLLASCWIIVRSSPTPGSEGHSAAPDCPSCALAALPKDVPNSQPEMVEAVK
KHILNMLHLKKRPDVTQPVPKAALLNAIRKLHVGKVGENGYVEIEDDIGRRAEMNELMEQ
TSEIITFAESGTARKTLHFEISKEGSDLSVVERAEVWLFLKVPKANRTRTKVTIRLFQQQK
HPQGSLDTGEEAEEVGLKGERSELLLSEKVVDARKSTWHVFPVSSSIQRLLDQGKSSLD
VRIACEQCQESGASLVLLGKKKKKEEEGEGKKKGGGEGGAGADEEKEQSHRPFLMLQA
RQSEDHPHRRRRRGLECDGKVNICCKKQFFVSFKDIGWNDWIIAPSGYHANYCEGECP
SHIAGTSGSSLSFHSTVINHYRMRGHSPFANLKSCCVPTKLRPMSMLYYDDGQNIIKKDI
QNMIVEECGCS (SEQ ID NO: 5)

FIG. 5

MESKGASSCRLLFCLLISATVFRPGLGWYTVNSAYGDTIIIPCRLDVPQNLMFGKWKYEK
PDGSPVFIAFRSSTKKSVQYDDVPEYKDRLNLSENYTLSISNARISDEKRFVCMLVTEDN
VFEAPTIVKVFSK (SEQ ID NO: 6)

FIG. 6

MELDRAVGVLGAATLLLSFLGMAWALQAADTCPEVKMVGLEGSDKLTILRGCPGLPGAPG
DKGEAGTNGKRGERGPPGPPGKAGPPGPNGAPGEPQPCLTGPRTCKDLLDRGHFLSG
WHTIYLPDCRPLTVLCDMDTDGGGWTVFQRRVDGSVDFYRDWATYKQGFGSRLGEFWL
GNDNIHALTAQGTSELRVDLVDFEDNYQFAKYRSFKVADEAEKYNLVLGAFVEGSAGDSLT
FHNNQSFSTKDQDNDLNTGNCAVMFQGAWWYKNCHVSNLNGRYLRGTHGSFANGINW
KSGKGYNYSYKVSEMKVRPA (SEQ ID NO: 7)

SEQUENCE LISTING

```
<160> NUMBER OF SEQ ID NOS: 7

<210> SEQ ID NO 1
<211> LENGTH: 267
<212> TYPE: PRT
<213> ORGANISM: Homo sapiens

<400> SEQUENCE: 1

Met Arg Leu Thr Val Leu Cys Ala Val Cys Leu Leu Pro Gly Ser Leu
1               5                   10                  15

Ala Leu Pro Leu Pro Gln Glu Ala Gly Gly Met Ser Glu Leu Gln Trp
            20                  25                  30

Glu Gln Ala Gln Asp Tyr Leu Lys Arg Phe Tyr Leu Tyr Asp Ser Glu
        35                  40                  45

Thr Lys Asn Ala Asn Ser Leu Glu Ala Lys Leu Lys Glu Met Gln Lys
    50                  55                  60

Phe Phe Gly Leu Pro Ile Thr Gly Met Leu Asn Ser Arg Val Ile Glu
65                  70                  75                  80

Ile Met Gln Lys Pro Arg Cys Gly Val Pro Asp Val Ala Glu Tyr Ser
                85                  90                  95

Leu Phe Pro Asn Ser Pro Lys Trp Thr Ser Lys Val Val Thr Tyr Arg
            100                 105                 110

Ile Val Ser Tyr Thr Arg Asp Leu Pro His Ile Thr Val Asp Arg Leu
        115                 120                 125

Val Ser Lys Ala Leu Asn Met Trp Gly Lys Glu Ile Pro Leu His Phe
    130                 135                 140

Arg Lys Val Val Trp Gly Thr Ala Asp Ile Met Ile Gly Phe Ala Arg
145                 150                 155                 160

Gly Ala His Gly Asp Ser Tyr Pro Phe Asp Gly Pro Gly Asn Thr Leu
                165                 170                 175

Ala His Ala Phe Ala Pro Gly Thr Gly Leu Gly Gly Asp Ala His Phe
            180                 185                 190

Asp Glu Asp Glu Arg Trp Thr Asp Gly Ser Ser Leu Gly Ile Asn Phe
        195                 200                 205

Leu Tyr Ala Ala Thr His Glu Leu Gly His Ser Leu Gly Met Gly His
    210                 215                 220
```

```
Ser Ser Asp Pro Asn Ala Val Met Tyr Pro Thr Tyr Gly Asn Gly Asp
225                 230                 235                 240

Pro Gln Asn Phe Lys Leu Ser Gln Asp Asp Ile Lys Gly Ile Gln Lys
            245                 250                 255

Leu Tyr Gly Lys Arg Ser Asn Ser Arg Lys Lys
        260                 265

<210> SEQ ID NO 2
<211> LENGTH: 1039
<212> TYPE: PRT
<213> ORGANISM: Homo sapiens

<400> SEQUENCE: 2

Met Ala Arg Ala Leu Cys Pro Leu Gln Ala Leu Trp Leu Leu Glu Trp
1               5                   10                  15

Val Leu Leu Leu Leu Gly Ala Cys Ala Ala Pro Pro Ala Trp Ala Leu
                20                  25                  30

Asn Leu Asp Pro Val Gln Leu Thr Phe Tyr Ala Gly Pro Asn Gly Ser
            35                  40                  45

Gln Phe Gly Phe Ser Leu Asp Phe His Lys Asp Ser His Gly Arg Val
    50                  55                  60

Ala Ile Val Val Gly Ala Pro Arg Thr Leu Gly Pro Ser Gln Glu Glu
65                  70                  75                  80

Thr Gly Gly Val Phe Leu Cys Pro Trp Arg Ala Glu Gly Gly Gln Cys
                85                  90                  95

Pro Ser Leu Leu Phe Asp Leu Arg Asp Glu Thr Arg Asn Val Gly Ser
            100                 105                 110

Gln Thr Leu Gln Thr Phe Lys Ala Arg Gln Gly Leu Gly Ala Ser Val
    115                 120                 125

Val Ser Trp Ser Asp Val Ile Val Ala Cys Ala Pro Trp Gln His Trp
130                 135                 140

Asn Val Leu Glu Lys Thr Glu Glu Ala Glu Lys Thr Pro Val Gly Ser
145                 150                 155                 160

Cys Phe Leu Ala Gln Pro Glu Ser Gly Arg Arg Ala Glu Tyr Ser Pro
                165                 170                 175

Cys Arg Gly Asn Thr Leu Ser Arg Ile Tyr Val Glu Asn Asp Phe Ser
            180                 185                 190

Trp Asp Lys Arg Tyr Cys Glu Ala Gly Phe Ser Ser Val Val Thr Gln
    195                 200                 205

Ala Gly Glu Leu Val Leu Gly Ala Pro Gly Gly Tyr Tyr Phe Leu Gly
210                 215                 220

Leu Leu Ala Gln Ala Pro Val Ala Asp Ile Phe Ser Ser Tyr Arg Pro
225                 230                 235                 240

Gly Ile Leu Leu Trp His Val Ser Gln Ser Leu Ser Phe Asp Ser Ser
                245                 250                 255

Ser Asn Pro Glu Tyr Phe Asp Gly Tyr Trp Gly Tyr Ser Val Ala Val
            260                 265                 270

Gly Glu Phe Asp Gly Asp Leu Asn Thr Thr Glu Tyr Val Val Gly Ala
    275                 280                 285

Pro Thr Trp Ser Trp Thr Leu Gly Ala Val Glu Ile Leu Asp Ser Tyr
290                 295                 300

Tyr Gln Arg Leu His Arg Leu Arg Ala Glu Gln Met Ala Ser Tyr Phe
305                 310                 315                 320

Gly His Ser Val Ala Val Thr Asp Val Asn Gly Asp Gly Arg His Asp
                325                 330                 335
```

-continued

```
Leu Leu Val Gly Ala Pro Leu Tyr Met Asp Ser Arg Ala Asp Arg Lys
            340                 345                 350

Leu Ala Glu Val Gly Arg Val Tyr Leu Phe Leu Gln Pro Arg Gly Pro
        355                 360                 365

His Ala Leu Gly Ala Pro Ser Leu Leu Leu Thr Gly Thr Gln Leu Tyr
    370                 375                 380

Gly Arg Phe Gly Ser Ala Ile Ala Pro Leu Gly Asp Leu Asp Arg Asp
385                 390                 395                 400

Gly Tyr Asn Asp Ile Ala Val Ala Ala Pro Tyr Gly Gly Pro Ser Gly
                405                 410                 415

Arg Gly Gln Val Leu Val Phe Leu Gly Gln Ser Glu Gly Leu Arg Ser
            420                 425                 430

Arg Pro Ser Gln Val Leu Asp Ser Pro Phe Pro Thr Gly Ser Ala Phe
        435                 440                 445

Gly Phe Ser Leu Arg Gly Ala Val Asp Ile Asp Asn Gly Tyr Pro
    450                 455                 460

Asp Leu Ile Val Gly Ala Tyr Gly Ala Asn Gln Val Ala Val Tyr Arg
465                 470                 475                 480

Ala Gln Pro Val Val Lys Ala Ser Val Gln Leu Leu Val Gln Asp Ser
                485                 490                 495

Leu Asn Pro Ala Val Lys Ser Cys Val Leu Pro Gln Thr Lys Thr Pro
            500                 505                 510

Val Ser Cys Phe Asn Ile Gln Met Cys Val Gly Ala Thr Gly His Asn
        515                 520                 525

Ile Pro Gln Lys Leu Ser Leu Asn Ala Glu Leu Gln Leu Asp Arg Gln
    530                 535                 540

Lys Pro Arg Gln Gly Arg Val Leu Leu Leu Gly Ser Gln Gln Ala
545                 550                 555                 560

Gly Thr Thr Leu Asp Leu Asp Leu Gly Gly Lys His Ser Pro Ile Cys
                565                 570                 575

His Thr Thr Met Ala Phe Leu Arg Asp Glu Ala Asp Phe Arg Asp Lys
            580                 585                 590

Leu Ser Pro Ile Val Leu Ser Leu Asn Val Ser Leu Pro Pro Thr Glu
        595                 600                 605

Ala Gly Met Ala Pro Ala Val Val Leu His Gly Asp Thr His Val Gln
    610                 615                 620

Glu Gln Thr Arg Ile Val Leu Asp Cys Gly Glu Asp Val Cys Val
625                 630                 635                 640

Pro Gln Leu Gln Leu Thr Ala Ser Val Thr Gly Ser Pro Leu Leu Val
                645                 650                 655

Gly Ala Asp Asn Val Leu Glu Leu Gln Met Asp Ala Ala Asn Glu Gly
            660                 665                 670

Glu Gly Ala Tyr Glu Ala Glu Leu Ala Val His Leu Pro Gln Gly Ala
        675                 680                 685

His Tyr Met Arg Ala Leu Ser Asn Val Glu Gly Phe Glu Arg Leu Ile
    690                 695                 700

Cys Asn Gln Lys Lys Glu Asn Glu Thr Arg Val Val Leu Cys Glu Leu
705                 710                 715                 720

Gly Asn Pro Met Lys Lys Asn Ala Gln Ile Gly Ile Ala Met Leu Val
                725                 730                 735

Ser Val Gly Asn Leu Glu Glu Ala Gly Glu Ser Val Ser Phe Gln Leu
            740                 745                 750
```

```
Gln Ile Arg Ser Lys Asn Ser Gln Asn Pro Asn Ser Lys Ile Val Leu
            755                 760                 765

Leu Asp Val Pro Val Arg Ala Glu Ala Gln Val Glu Leu Arg Gly Asn
770                 775                 780

Ser Phe Pro Ala Ser Leu Val Val Ala Ala Glu Glu Gly Arg Glu
785                 790                 795                 800

Gln Asn Ser Leu Asp Ser Trp Gly Pro Lys Val Glu His Thr Tyr Glu
                805                 810                 815

Leu His Asn Asn Gly Pro Gly Thr Val Asn Gly Leu His Leu Ser Ile
            820                 825                 830

His Leu Pro Gly Gln Ser Gln Pro Ser Asp Leu Leu Tyr Ile Leu Asp
        835                 840                 845

Ile Gln Pro Gln Gly Gly Leu Gln Cys Phe Pro Gln Pro Val Asn
    850                 855                 860

Pro Leu Lys Val Asp Trp Gly Leu Pro Ile Pro Ser Pro Ser Pro Ile
865                 870                 875                 880

His Pro Ala His His Lys Arg Asp Arg Gln Ile Phe Leu Pro Glu
                885                 890                 895

Pro Glu Gln Pro Ser Arg Leu Gln Asp Pro Val Leu Val Ser Cys Asp
            900                 905                 910

Ser Ala Pro Cys Thr Val Val Gln Cys Asp Leu Gln Glu Met Ala Arg
        915                 920                 925

Gly Gln Arg Ala Met Val Thr Val Leu Ala Phe Leu Trp Leu Pro Ser
    930                 935                 940

Leu Tyr Gln Arg Pro Leu Asp Gln Phe Val Leu Gln Ser His Ala Trp
945                 950                 955                 960

Phe Asn Val Ser Ser Leu Pro Tyr Ala Val Pro Pro Leu Ser Leu Pro
                965                 970                 975

Arg Gly Glu Ala Gln Val Trp Thr Gln Leu Leu Arg Ala Leu Glu Glu
            980                 985                 990

Arg Ala Ile Pro Ile Trp Trp Val Leu Val Gly Val Leu Gly Gly Leu
        995                 1000                1005

Leu Leu Leu Thr Ile Leu Val Leu Ala Met Trp Lys Val Gly Phe
    1010                1015                1020

Phe Lys Arg Asn Arg His Thr Leu Glu Glu Asp Asp Glu Glu Gly
    1025                1030                1035

Glu

<210> SEQ ID NO 3
<211> LENGTH: 788
<212> TYPE: PRT
<213> ORGANISM: Homo sapiens

<400> SEQUENCE: 3

Met Arg Ala Arg Pro Arg Pro Arg Pro Leu Trp Val Thr Val Leu Ala
1               5                   10                  15

Leu Gly Ala Leu Ala Gly Val Gly Val Gly Gly Pro Asn Ile Cys Thr
                20                  25                  30

Thr Arg Gly Val Ser Ser Cys Gln Gln Cys Leu Ala Val Ser Pro Met
            35                  40                  45

Cys Ala Trp Cys Ser Asp Glu Ala Leu Pro Leu Gly Ser Pro Arg Cys
    50                  55                  60

Asp Leu Lys Glu Asn Leu Leu Lys Asp Asn Cys Ala Pro Glu Ser Ile
65                  70                  75                  80
```

```
Glu Phe Pro Val Ser Glu Ala Arg Val Leu Glu Asp Arg Pro Leu Ser
                 85                  90                  95

Asp Lys Gly Ser Gly Asp Ser Ser Gln Val Thr Gln Val Ser Pro Gln
            100                 105                 110

Arg Ile Ala Leu Arg Leu Arg Pro Asp Asp Ser Lys Asn Phe Ser Ile
        115                 120                 125

Gln Val Arg Gln Val Glu Asp Tyr Pro Val Asp Ile Tyr Tyr Leu Met
    130                 135                 140

Asp Leu Ser Tyr Ser Met Lys Asp Asp Leu Trp Ser Ile Gln Asn Leu
145                 150                 155                 160

Gly Thr Lys Leu Ala Thr Gln Met Arg Lys Leu Thr Ser Asn Leu Arg
                165                 170                 175

Ile Gly Phe Gly Ala Phe Val Asp Lys Pro Val Ser Pro Tyr Met Tyr
            180                 185                 190

Ile Ser Pro Pro Glu Ala Leu Glu Asn Pro Cys Tyr Asp Met Lys Thr
        195                 200                 205

Thr Cys Leu Pro Met Phe Gly Tyr Lys His Val Leu Thr Leu Thr Asp
    210                 215                 220

Gln Val Thr Arg Phe Asn Glu Glu Val Lys Lys Gln Ser Val Ser Arg
225                 230                 235                 240

Asn Arg Asp Ala Pro Glu Gly Gly Phe Asp Ala Ile Met Gln Ala Thr
                245                 250                 255

Val Cys Asp Glu Lys Ile Gly Trp Arg Asn Asp Ala Ser His Leu Leu
            260                 265                 270

Val Phe Thr Thr Asp Ala Lys Thr His Ile Ala Leu Asp Gly Arg Leu
        275                 280                 285

Ala Gly Ile Val Gln Pro Asn Asp Gly Gln Cys His Val Gly Ser Asp
    290                 295                 300

Asn His Tyr Ser Ala Ser Thr Thr Met Asp Tyr Pro Ser Leu Gly Leu
305                 310                 315                 320

Met Thr Glu Lys Leu Ser Gln Lys Asn Ile Asn Leu Ile Phe Ala Val
                325                 330                 335

Thr Glu Asn Val Val Asn Leu Tyr Gln Asn Tyr Ser Glu Leu Ile Pro
            340                 345                 350

Gly Thr Thr Val Gly Val Leu Ser Met Asp Ser Ser Asn Val Leu Gln
        355                 360                 365

Leu Ile Val Asp Ala Tyr Gly Lys Ile Arg Ser Lys Val Glu Leu Glu
    370                 375                 380

Val Arg Asp Leu Pro Glu Glu Leu Ser Leu Ser Phe Asn Ala Thr Cys
385                 390                 395                 400

Leu Asn Asn Glu Val Ile Pro Gly Leu Lys Ser Cys Met Gly Leu Lys
                405                 410                 415

Ile Gly Asp Thr Val Ser Phe Ser Ile Glu Ala Lys Val Arg Gly Cys
            420                 425                 430

Pro Gln Glu Lys Glu Lys Ser Phe Thr Ile Lys Pro Val Gly Phe Lys
        435                 440                 445

Asp Ser Leu Ile Val Gln Val Thr Phe Asp Cys Asp Cys Ala Cys Gln
    450                 455                 460

Ala Gln Ala Glu Pro Asn Ser His Arg Cys Asn Asn Gly Asn Gly Thr
465                 470                 475                 480

Phe Glu Cys Gly Val Cys Arg Cys Gly Pro Gly Trp Leu Gly Ser Gln
                485                 490                 495
```

```
Cys Glu Cys Ser Glu Glu Asp Tyr Arg Pro Ser Gln Gln Asp Glu Cys
                500                 505                 510
Ser Pro Arg Glu Gly Gln Pro Val Cys Ser Gln Arg Gly Glu Cys Leu
            515                 520                 525
Cys Gly Gln Cys Val Cys His Ser Ser Asp Phe Gly Lys Ile Thr Gly
        530                 535                 540
Lys Tyr Cys Glu Cys Asp Asp Phe Ser Cys Val Arg Tyr Lys Gly Glu
545                 550                 555                 560
Met Cys Ser Gly His Gly Gln Cys Ser Cys Gly Asp Cys Leu Cys Asp
                565                 570                 575
Ser Asp Trp Thr Gly Tyr Tyr Cys Asn Cys Thr Thr Arg Thr Asp Thr
            580                 585                 590
Cys Met Ser Ser Asn Gly Leu Leu Cys Ser Gly Arg Gly Lys Cys Glu
        595                 600                 605
Cys Gly Ser Cys Val Cys Ile Gln Pro Gly Ser Tyr Gly Asp Thr Cys
        610                 615                 620
Glu Lys Cys Pro Thr Cys Pro Asp Ala Cys Thr Phe Lys Lys Glu Cys
625                 630                 635                 640
Val Glu Cys Lys Lys Phe Asp Arg Glu Pro Tyr Met Thr Glu Asn Thr
                645                 650                 655
Cys Asn Arg Tyr Cys Arg Asp Glu Ile Glu Ser Val Lys Glu Leu Lys
            660                 665                 670
Asp Thr Gly Lys Asp Ala Val Asn Cys Thr Tyr Lys Asn Glu Asp Asp
        675                 680                 685
Cys Val Val Arg Phe Gln Tyr Tyr Glu Asp Ser Ser Gly Lys Ser Ile
        690                 695                 700
Leu Tyr Val Val Glu Glu Pro Glu Cys Pro Lys Gly Pro Asp Ile Leu
705                 710                 715                 720
Val Val Leu Leu Ser Val Met Gly Ala Ile Leu Leu Ile Gly Leu Ala
                725                 730                 735
Ala Leu Leu Ile Trp Lys Leu Leu Ile Thr Ile His Asp Arg Lys Glu
            740                 745                 750
Phe Ala Lys Phe Glu Glu Glu Arg Ala Arg Ala Lys Trp Asp Thr Ala
        755                 760                 765
Asn Asn Pro Leu Tyr Lys Glu Ala Thr Ser Thr Phe Thr Asn Ile Thr
        770                 775                 780
Tyr Arg Gly Thr
785

<210> SEQ ID NO 4
<211> LENGTH: 342
<212> TYPE: PRT
<213> ORGANISM: Homo sapiens

<400> SEQUENCE: 4

Met Leu Pro Leu Leu Leu Pro Leu Leu Trp Ala Gly Ala Leu Ala Gln
1               5                   10                  15
Glu Arg Arg Phe Gln Leu Glu Gly Pro Glu Ser Leu Thr Val Gln Glu
            20                  25                  30
Gly Leu Cys Val Leu Val Pro Cys Arg Leu Pro Thr Thr Leu Pro Ala
        35                  40                  45
Ser Tyr Tyr Gly Tyr Gly Tyr Trp Phe Leu Glu Gly Ala Asp Val Pro
    50                  55                  60
Val Ala Thr Asn Asp Pro Asp Glu Glu Val Gln Glu Glu Thr Arg Gly
65                  70                  75                  80
```

```
Arg Phe His Leu Leu Trp Asp Pro Arg Lys Asn Cys Ser Leu Ser
                85                  90                  95

Ile Arg Asp Ala Arg Arg Asp Asn Ala Ala Tyr Phe Phe Arg Leu
            100                 105                 110

Lys Ser Lys Trp Met Lys Tyr Gly Tyr Thr Ser Ser Lys Leu Ser Val
            115                 120                 125

Arg Val Met Ala Leu Thr His Arg Pro Asn Ile Ser Ile Pro Gly Thr
            130                 135                 140

Leu Glu Ser Gly His Pro Ser Asn Leu Thr Cys Ser Val Pro Trp Val
145                 150                 155                 160

Cys Glu Gln Gly Thr Pro Pro Ile Phe Ser Trp Met Ser Ala Ala Pro
                165                 170                 175

Thr Ser Leu Gly Pro Arg Thr Thr Gln Ser Ser Val Leu Thr Ile Thr
                180                 185                 190

Pro Arg Pro Gln Asp His Ser Thr Asn Leu Thr Cys Gln Val Thr Phe
            195                 200                 205

Pro Gly Ala Gly Val Thr Met Glu Arg Thr Ile Gln Leu Asn Val Ser
            210                 215                 220

Tyr Ala Pro Gln Lys Val Ala Ile Ser Ile Phe Gln Gly Asn Ser Ala
225                 230                 235                 240

Ala Phe Lys Ile Leu Gln Asn Thr Ser Ser Leu Pro Val Leu Glu Gly
                245                 250                 255

Gln Ala Leu Arg Leu Leu Cys Asp Ala Asp Gly Asn Pro Pro Ala His
                260                 265                 270

Leu Ser Trp Phe Gln Gly Phe Pro Ala Leu Asn Ala Thr Pro Ile Ser
                275                 280                 285

Asn Thr Gly Val Leu Glu Leu Pro Gln Val Gly Ser Ala Glu Glu Gly
            290                 295                 300

Asp Phe Thr Cys Arg Ala Gln His Pro Leu Gly Ser Leu Gln Ile Ser
305                 310                 315                 320

Leu Ser Leu Phe Val His Trp Ser Ser Ala Pro Val Pro Asp Arg His
                325                 330                 335

Ser Phe Arg Pro Pro Cys
            340

<210> SEQ ID NO 5
<211> LENGTH: 426
<212> TYPE: PRT
<213> ORGANISM: Homo sapiens

<400> SEQUENCE: 5

Met Pro Leu Leu Trp Leu Arg Gly Phe Leu Leu Ala Ser Cys Trp Ile
1               5                   10                  15

Ile Val Arg Ser Ser Pro Thr Pro Gly Ser Glu Gly His Ser Ala Ala
            20                  25                  30

Pro Asp Cys Pro Ser Cys Ala Leu Ala Ala Leu Pro Lys Asp Val Pro
            35                  40                  45

Asn Ser Gln Pro Glu Met Val Glu Ala Val Lys Lys His Ile Leu Asn
        50                  55                  60

Met Leu His Leu Lys Lys Arg Pro Asp Val Thr Gln Pro Val Pro Lys
65                  70                  75                  80

Ala Ala Leu Leu Asn Ala Ile Arg Lys Leu His Val Gly Lys Val Gly
                85                  90                  95

Glu Asn Gly Tyr Val Glu Ile Glu Asp Asp Ile Gly Arg Arg Ala Glu
            100                 105                 110
```

```
Met Asn Glu Leu Met Glu Gln Thr Ser Glu Ile Ile Thr Phe Ala Glu
            115                 120                 125

Ser Gly Thr Ala Arg Lys Thr Leu His Phe Glu Ile Ser Lys Glu Gly
        130                 135                 140

Ser Asp Leu Ser Val Val Glu Arg Ala Glu Val Trp Leu Phe Leu Lys
145                 150                 155                 160

Val Pro Lys Ala Asn Arg Thr Arg Thr Lys Val Thr Ile Arg Leu Phe
                165                 170                 175

Gln Gln Gln Lys His Pro Gln Gly Ser Leu Asp Thr Gly Glu Glu Ala
            180                 185                 190

Glu Glu Val Gly Leu Lys Gly Glu Arg Ser Glu Leu Leu Leu Ser Glu
        195                 200                 205

Lys Val Val Asp Ala Arg Lys Ser Thr Trp His Val Phe Pro Val Ser
210                 215                 220

Ser Ser Ile Gln Arg Leu Leu Asp Gln Gly Lys Ser Ser Leu Asp Val
225                 230                 235                 240

Arg Ile Ala Cys Glu Gln Cys Gln Glu Ser Gly Ala Ser Leu Val Leu
                245                 250                 255

Leu Gly Lys Lys Lys Lys Lys Glu Glu Glu Gly Glu Gly Lys Lys Lys
            260                 265                 270

Gly Gly Gly Glu Gly Gly Ala Gly Ala Asp Glu Glu Lys Glu Gln Ser
        275                 280                 285

His Arg Pro Phe Leu Met Leu Gln Ala Arg Gln Ser Glu Asp His Pro
            290                 295                 300

His Arg Arg Arg Arg Gly Leu Glu Cys Asp Gly Lys Val Asn Ile
305                 310                 315                 320

Cys Cys Lys Lys Gln Phe Phe Val Ser Phe Lys Asp Ile Gly Trp Asn
                325                 330                 335

Asp Trp Ile Ile Ala Pro Ser Gly Tyr His Ala Asn Tyr Cys Glu Gly
            340                 345                 350

Glu Cys Pro Ser His Ile Ala Gly Thr Ser Gly Ser Ser Leu Ser Phe
        355                 360                 365

His Ser Thr Val Ile Asn His Tyr Arg Met Arg Gly His Ser Pro Phe
    370                 375                 380

Ala Asn Leu Lys Ser Cys Cys Val Pro Thr Lys Leu Arg Pro Met Ser
385                 390                 395                 400

Met Leu Tyr Tyr Asp Asp Gly Gln Asn Ile Ile Lys Lys Asp Ile Gln
                405                 410                 415

Asn Met Ile Val Glu Glu Cys Gly Cys Ser
            420                 425

<210> SEQ ID NO 6
<211> LENGTH: 133
<212> TYPE: PRT
<213> ORGANISM: Homo sapiens

<400> SEQUENCE: 6

Met Glu Ser Lys Gly Ala Ser Ser Cys Arg Leu Leu Phe Cys Leu Leu
1               5                   10                  15

Ile Ser Ala Thr Val Phe Arg Pro Gly Leu Gly Trp Tyr Thr Val Asn
                20                  25                  30

Ser Ala Tyr Gly Asp Thr Ile Ile Pro Cys Arg Leu Asp Val Pro
            35                  40                  45

Gln Asn Leu Met Phe Gly Lys Trp Lys Tyr Glu Lys Pro Asp Gly Ser
        50                  55                  60
```

```
Pro Val Phe Ile Ala Phe Arg Ser Ser Thr Lys Ser Val Gln Tyr
 65                  70                  75                  80

Asp Asp Val Pro Glu Tyr Lys Asp Arg Leu Asn Leu Ser Glu Asn Tyr
                 85                  90                  95

Thr Leu Ser Ile Ser Asn Ala Arg Ile Ser Asp Glu Lys Arg Phe Val
            100                 105                 110

Cys Met Leu Val Thr Glu Asp Asn Val Phe Glu Ala Pro Thr Ile Val
            115                 120                 125

Lys Val Phe Ser Lys
            130
```

<210> SEQ ID NO 7
<211> LENGTH: 313
<212> TYPE: PRT
<213> ORGANISM: Homo sapiens

<400> SEQUENCE: 7

```
Met Glu Leu Asp Arg Ala Val Gly Val Leu Gly Ala Ala Thr Leu Leu
  1               5                  10                  15

Leu Ser Phe Leu Gly Met Ala Trp Ala Leu Gln Ala Ala Asp Thr Cys
             20                  25                  30

Pro Glu Val Lys Met Val Gly Leu Glu Gly Ser Asp Lys Leu Thr Ile
             35                  40                  45

Leu Arg Gly Cys Pro Gly Leu Pro Gly Ala Pro Gly Asp Lys Gly Glu
         50                  55                  60

Ala Gly Thr Asn Gly Lys Arg Gly Glu Arg Gly Pro Pro Gly Pro Pro
 65                  70                  75                  80

Gly Lys Ala Gly Pro Pro Gly Pro Asn Gly Ala Pro Gly Glu Pro Gln
                 85                  90                  95

Pro Cys Leu Thr Gly Pro Arg Thr Cys Lys Asp Leu Leu Asp Arg Gly
            100                 105                 110

His Phe Leu Ser Gly Trp His Thr Ile Tyr Leu Pro Asp Cys Arg Pro
            115                 120                 125

Leu Thr Val Leu Cys Asp Met Asp Thr Asp Gly Gly Gly Trp Thr Val
            130                 135                 140

Phe Gln Arg Arg Val Asp Gly Ser Val Asp Phe Tyr Arg Asp Trp Ala
145                 150                 155                 160

Thr Tyr Lys Gln Gly Phe Gly Ser Arg Leu Gly Glu Phe Trp Leu Gly
                165                 170                 175

Asn Asp Asn Ile His Ala Leu Thr Ala Gln Gly Thr Ser Glu Leu Arg
            180                 185                 190

Val Asp Leu Val Asp Phe Glu Asp Asn Tyr Gln Phe Ala Lys Tyr Arg
            195                 200                 205

Ser Phe Lys Val Ala Asp Glu Ala Glu Lys Tyr Asn Leu Val Leu Gly
            210                 215                 220

Ala Phe Val Glu Gly Ser Ala Gly Asp Ser Leu Thr Phe His Asn Asn
225                 230                 235                 240

Gln Ser Phe Ser Thr Lys Asp Gln Asp Asn Asp Leu Asn Thr Gly Asn
                245                 250                 255

Cys Ala Val Met Phe Gln Gly Ala Trp Trp Tyr Lys Asn Cys His Val
            260                 265                 270

Ser Asn Leu Asn Gly Arg Tyr Leu Arg Gly Thr His Gly Ser Phe Ala
            275                 280                 285
```

```
Asn Gly Ile Asn Trp Lys Ser Gly Lys Gly Tyr Asn Tyr Ser Tyr Lys
    290                 295                 300

Val Ser Glu Met Lys Val Arg Pro Ala
305                 310
```

KITS AND METHODS FOR PREDICTION AND TREATMENT OF PREECLAMPSIA

CROSS-REFERENCE TO RELATED APPLICATIONS

This application is a U.S. National Phase Application based on International Patent Application No. PCT/US2016/060825, which was filed on Nov. 7, 2016, which claims priority to U.S. Provisional Patent Application No. 62/251,589 filed on Nov. 5, 2015, each of which are incorporated herein by reference in their entirety as if fully set forth herein.

STATEMENT REGARDING FEDERALLY SPONSORED RESEARCH

This invention was made with government support under grant NICHD grant HSN275201300006C awarded by the National Institute of Child Health and Human Development. The government has certain rights in the invention.

FIELD OF THE DISCLOSURE

The present disclosure provides kits and methods for the early prediction of preeclampsia. More specifically, the kits and methods can utilize measurement of the levels of six markers, including Matrilysin (MMP-7), Integrin alpha-IIb: beta-3 complex (gpIIbIIIa), Sialic acid-binding Ig-like lectin 6 (Siglec-6), Activin A, ALCAM, and/or Ficolin-2 (FCN2).

BACKGROUND OF THE DISCLOSURE

Preeclampsia is a syndrome defined by pregnancy-induced hypertension and proteinuria, which can lead to eclampsia (convulsions), and other serious maternal and/or fetal complications. Preeclampsia originates in early gestation from the failure of implantation mechanisms and/or placental development, and is thus closely related to complications of pregnancy in early gestation such as implantation failure, and threatened and spontaneous miscarriage, Preeclampsia affects 5-7% of pregnant women (8,370,000 pregnant women worldwide per year) and is a major cause of maternal and perinatal mortality. Furthermore, women with preeclampsia have an 8-fold higher risk of cardiovascular death later in their life, and offspring born from pregnancies affected by preeclampsia have an increased risk of metabolic and cardiovascular disease and mortality later in life.

The present diagnostic criteria for preeclampsia set by the United States National High Blood Pressure Education Program Working Group on High Blood Pressure in Pregnancy include new-onset hypertension coupled with proteinuria that develops after 20 weeks of gestation in women with previously normal blood pressures. These criteria further define preeclampsia as systolic or diastolic blood pressures of ≥140 and/or ≥90 mmHg, respectively, measured at two or more different time points, at least 4 hours (h) but not more than 1 week apart, as well as proteinuria of ≥300 mg protein in a 24 h urine sample, or two random urine specimens obtained at least 4 h but not more than 1 week apart containing ≥1+ protein on a dipstick. Another sign of preeclampsia is maternal vascular underperfusion (MVU), which is a pathologic state of the placenta wherein maternal blood flow to the placenta is decreased.

Based on the timing of the clinical manifestation, preeclampsia has been historically classified into different subforms, such as "term" (≥37 weeks) and "preterm" (<37 weeks) or by using an alternative terminology "late-onset" and "early-onset" preeclampsia. Preeclampsia that develops during 34 weeks of gestational age or earlier can be referred to as early-onset preeclampsia. Late-onset preeclampsia can be defined as preeclampsia that develops after 34 weeks of gestational age, and it is important to note that preeclampsia may occur intrapartum or postpartum. Thus, monitoring and evaluating the symptoms of preeclampsia should be continued during the postpartum period.

SUMMARY OF THE DISCLOSURE

The present disclosure provides kits and method that allow for the prediction of preeclampsia. The kits and methods may also allow the prediction of closely related complications of pregnancy in early gestation such as implantation failure, and threatened and spontaneous miscarriage.

The current disclosure provides that six markers that can be found in maternal plasma can be used to predict the onset of preeclampsia. These preeclampsia markers include: Matrilysin (MMP-7), Integrin alpha-IIb: beta-3 complex (gpIIbIIIa), Sialic acid-binding Ig-like lectin 6 (Siglec-6), Activin A, ALCAM, and/or Ficolin-2 (FCN2).

In particular embodiments, the kits and methods are used for assessing the presence or risk of preeclampsia in a female to determine the need for a treatment regimen including: determining levels of one or more preeclampsia markers including; MMP-7, gpIIbIIIa, Siglec-6, Activin A, ALCAM, and/or FCN2 in a biological sample obtained from the female; generating a dataset based on the determined levels; assessing the presence or risk of developing preeclampsia in the female based on the dataset; and, in particular embodiments, determining a treatment regimen based on the assessed presence or risk.

In particular embodiments, the therapeutic intervention prevents, reduces, or delays symptoms of preeclampsia before the symptoms manifest in the female and/or fetus.

In particular embodiments kits for assessing the presence or risk of preeclampsia in a female to determine the need for a treatment regimen include: detection mechanisms for determining levels of one or more of MMP-7, gpIIbIIIa, Siglec-6, Activin A, ALCAM, and/or FCN2 in a biological sample obtained from the female; instructions how to (i) generate a dataset based on the determined levels; (ii) assess the presence or risk of developing preeclampsia in the female based on the dataset; and (iii) determine a treatment regimen based on the assessed presence or risk.

In particular embodiments, the kit includes detection mechanisms for at least 1, 2, 3, 4, 5, or 6 biomarkers. In particular embodiments, the kit includes detection mechanisms for all biomarkers described above.

BRIEF DESCRIPTION OF THE DRAWINGS

FIG. 1. An exemplary sequence of Matrilysin (MMP-7, SEQ ID NO: 1).

FIGS. 2A-2B. An exemplary sequence of Integrin alpha-IIb (gpIIb, FIG. 2A, SEQ ID NO: 2) and an exemplary sequence of Integrin beta-3 (gpIIIa, FIG. 2B, SEQ ID NO: 3).

FIG. 3. An exemplary sequence of Sialic acid-binding Ig-like lectin 6 (Siglec-6, SEQ ID NO: 4).

FIG. 4. An exemplary sequence of Activin A (SEQ ID NO: 5).

FIG. 5. An exemplary sequence of ALCAM (SEQ ID NO: 6).

FIG. 6. An exemplary sequence of Ficolin-2 (FCN2, SEQ ID NO: 7).

DETAILED DESCRIPTION

Figure 7A:
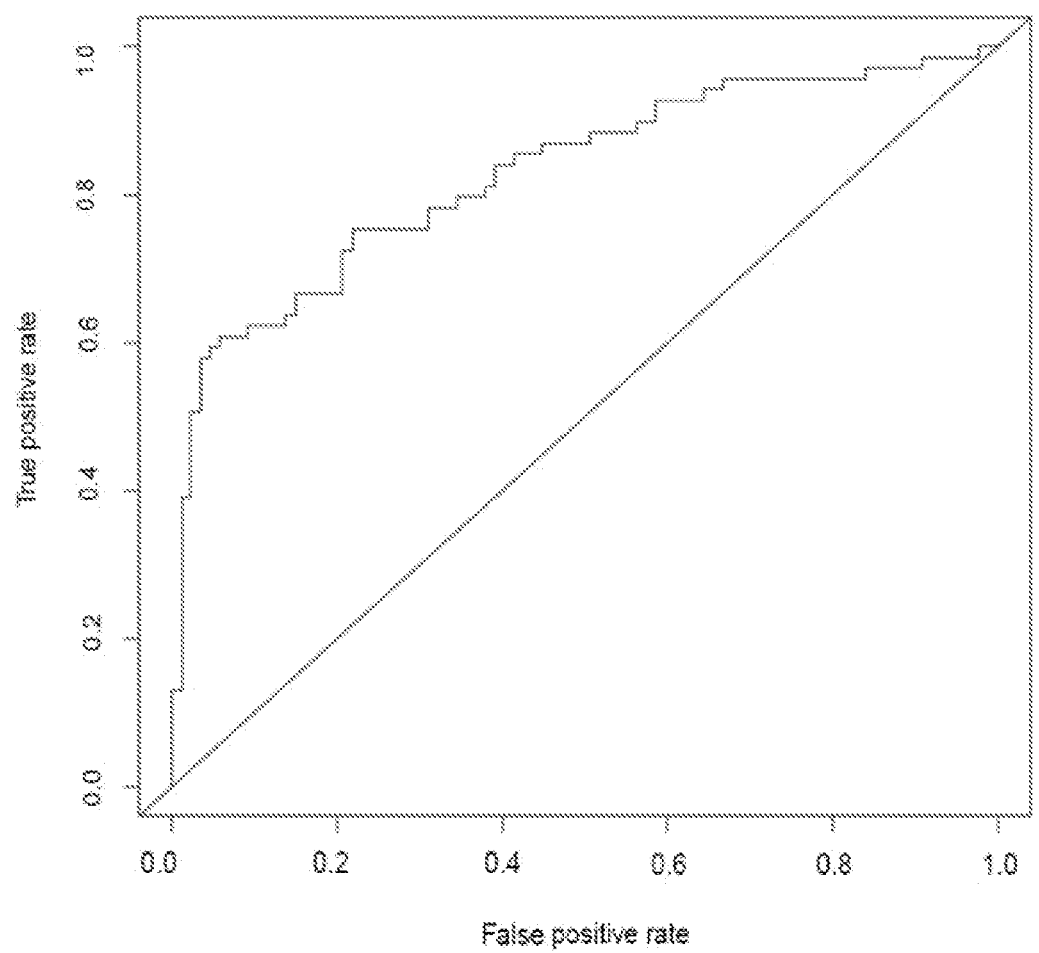
FIGS. 7A-7C. Receiver operating characteristic (ROC) curves for MMP-7 in patients with late preeclampsia (PE) with and without maternal vascular underperfusion (MVU) (FIG. 7A). Longitudinal profiles of maternal plasma MMP-7 (FIG. 7B) in patients with late PE with MVU (gray dots). The best interval for the discrimination between late PE MVU (dark gray dots) and controls is 16.1-22 weeks of gestation. Receiver operating characteristic (ROC) curves for MMP-7 in patients with MVU (FIG. 7C).

The present disclosure provides kits and methods to predict the onset of preeclampsia.

The disclosure provides that six markers in maternal plasma can be measured to predict the onset of preeclampsia. These markers include:

| Symbol | Name | UniProt ID | Outcome Predicted | GA (weeks) | AUC |
|---|---|---|---|---|---|
| MMP-7 | Matrilysin | P09237 | Early Preeclampsia | 16-22 | 0.89 |
| gpIIbIIIa | Integrin alpha-IIb: beta-3 complex | P08514/ P05106 | Early Preeclampsia | 16-22 | 0.84 |
| Siglec-6 | Sialic acid-binding Ig-like lectin 6 | O43699 | Early Preeclampsia | 22-28 | 0.91 |
| Activin A | Inhibin beta A chain | P08476 | Early Preeclampsia | 22-28 | 0.90 |
| ALCAM | CD166 antigen | Q13740 | Early Preeclampsia | 28-32 | 0.94 |
| Siglec-6 | Sialic acid-binding Ig-like lectin 6 | O43699 | Early Preeclampsia | 28-32 | 0.93 |
| FCN2 | Ficolin-2 | Q15485 | Early Preeclampsia | 28-32 | 0.92 |
| MMP-7 | Matrilysin | P09237 | Late Preeclampsia | 16-22 | 0.83 |
| Siglec-6 | Sialic acid-binding Ig-like lectin 6 | O43699 | Early Preeclampsia with MVU | 22-28 | 0.97 |

The present disclosure provides kits and method that allow for the prediction or detection of preeclampsia and may also allow the prediction of closely related complications of pregnancy in early gestation including implantation failure, and threatened and spontaneous miscarriage.

In particular embodiments, the kits and methods are used for assessing the presence or risk of preeclampsia in a female to determine the need for a treatment regimen including: determining levels of one or more preeclampsia markers including: MMP-7, gpIIbIIIa, Siglec-6, Activin A, ALCAM, and/or FCN2 in a biological sample obtained from the female; generating a dataset based on the determined levels; assessing the presence or risk of developing preeclampsia in the female based on the dataset; and, in particular embodiments, determining a treatment regimen based on the assessed presence or risk.

Compared to other technologies, methods described herein can identify women at risk of preeclampsia earlier in pregnancy (e.g., before 22 weeks of gestation). The methods described herein allow for better prediction performance in the same gestational age interval. For instance, a recent review and meta-analysis (Wu et al. (2015) Int J Mol Sci 16: 23035-23056) estimated the sensitivity of known single biomarkers for prediction of preeclampsia to be 40% at a false positive rate of 10% during the second trimester of pregnancy. The biomarkers described herein in this gestational age interval (16-22 weeks) has a sensitivity of 62% for late preeclampsia and 72% for early preeclampsia. Of note, these estimates of sensitivity are obtained assessed by bootstrap analysis, in which part of the sample set is not used in any way to identify the marker and evaluate its performance. The apparent sensitivity estimates (equivalent to those reported in Wu et al. (2015) Int J Mol Sci 16: 23035-23056) are even higher.

The test can be performed based on blood samples taken at regular prenatal care visits and can be used in assessing the risk for preeclampsia and other adverse pregnancy outcomes.

In particular embodiments, up to the 6 biomarkers described above are assessed at different dilution settings to allow obtaining concentration values instead of relative fluorescence data.

In particular embodiments, the kits and methods can utilize MMP-7 and gpIIaIIIb measurements from samples taken between the 16th and 22nd week of pregnancy to predict early onset preeclampsia.

In particular embodiments, the kits and methods can utilize MMP-7 measurements from samples taken between the 16th and 22nd week of pregnancy to predict late onset preeclampsia associated with MVU.

In particular embodiments, the kits and methods can utilize MMP-7 measurements taken during the 16th and $22^{nd}$ week of pregnancy to predict late onset preeclampsia.

In particular embodiments, the kits and methods can utilize Siglec-6 and Activin A measurements taken between the 22nd and 28th week of pregnancy to predict early onset preeclampsia.

In particular embodiments, the kits and methods can utilize Siglec-6 measurements taken between the 22nd and 28th week of pregnancy to predict early onset preeclampsia associated with MVU.

In particular embodiments, the kits and methods can utilize ALCAM, Siglec-6 and FCN2 measurements taken between the 28th and 32nd week of pregnancy to predict early onset preeclampsia.

In particular embodiments, the assaying is performed for the levels of at least or at least 1, 2, 3, 4, 5, or 6 biomarkers.

In particular embodiments, the sample is a blood sample or a serum sample. In particular embodiments the sample is another body fluid, secretion or excretion (such as cervicovaginal fluid, saliva, or urine).

In particular embodiments, the biological sample is obtained between the 16th and 22nd week of pregnancy. In particular embodiments, the biological sample is obtained between the 22nd and 28th week of pregnancy. In particular embodiments, the biological sample is obtained between the 28th and 32nd week of pregnancy In particular embodiments, protein levels of the preeclampsia markers are measured.

In particular embodiments, the preeclampsia markers can be measured using an array with wells or spots, wherein each well or spot contains a binding ligand that binds to a specific preeclampsia marker.

In particular embodiments, the kits and methods can predict preeclampsia with a specificity of at least 90%.

In particular embodiments, the treatment regimen is a therapeutic intervention.

In particular embodiments kits for assessing the presence or risk of preeclampsia in a female to determine the need for a treatment regimen include: detection mechanisms for determining levels of one or more of MMP-7, gpIIbIIIa, Siglec-6, Activin A, ALCAM, and/or FCN2 in a biological sample obtained from the female; instructions how to (i) generate a dataset based on the determined levels; (ii) assess the presence or risk of developing preeclampsia in the female based on the dataset; and (iii) determine a treatment regimen based on the assessed presence or risk.

In particular embodiments, the kit includes detection mechanisms for at least 1, 2, 3, 4, 5, or 6 biomarkers. In particular embodiments, the kit includes detection mechanisms for all biomarkers described above.

In particular embodiments, biomarker panel tests to predict preeclampsia can include measurement of MMP-7. MMP-7 (also known as uterine metalloproteinase) is a member of the matrix metalloproteinase protein family, which are calcium dependent, zinc binding endopeptidases. The function of MMP-7 includes degradation of the extracellular matrix. MMP-7 can be expressed by epithelial cells and secreted to cleave macromolecules including fibronectin, casein, proteoglycan, and certain types of collagen. In addition to endopeptidase activity, MMP-7 has been found to activate other matrix metalloproteinases, and is upregulated in certain malignant tumors. An exemplary sequence for MMP-7 (UniProt ID P09237) is GenBank accession number Z11887 (see FIG. 1, SEQ ID NO: 1).

In particular embodiments, biomarker panel tests to predict preeclampsia can include measurement of gpIIbIIIa (glycoprotein IIb/IIIa, also known as integrin αIIbβ3). GpIIbIIIa is expressed on the surface of platelets and is involved in platelet activation. Platelet activation induces a change in gpIIbIIIa that causes it to bind to fibrinogen, allowing individual platelets to connect and form a clot. GpIIbIIIa is a heterodimer of the subunits gpIIb (or integrin alpha IIb) and gpIIIa (or integrin beta 3). An exemplary sequence for gpIIb (UniProt ID P08514) is GenBank accession number M34480 (see FIG. 2A, SEQ ID NO: 2). An exemplary sequence for gpIIIa (UniProt ID P05106) is GenBank accession number J02703 (see FIG. 2B, SEQ ID NO: 3).

In particular embodiments, biomarker panel tests to predict preeclampsia can include measurement of Siglec-6 (also known as CD327, CD33L, CDW327). The Siglec (sialic acid-binding immunoglobulin-type lectin) protein family are membrane-bound proteins that bind to sialic acid. Siglec-6 is expressed on the surface of trophoblasts and upregulation of Siglec-6 in placental tissue is associated with pregnancy complications. An exemplary sequence for Siglec-6 (UniProt ID O43699) is GenBank accession number D86359 (see FIG. 3, SEQ ID NO: 4).

In particular embodiments, biomarker panel tests to predict preeclampsia can include measurement of Activin A. Activins are protein complexes that enhance follicle-stimulating hormone synthesis and secretion. Follicle-stimulating hormone is involved in ovulation in females and maturation of germ cells in both males and females. Activin A is a homodimer of two subunits of Activin Beta-A. Activin Beta-A can bind to other subunits to form heterodimers, such as Inhibin A and Activin AB. An exemplary sequence for Activin Beta-A (UniProt ID P08476) is GenBank accession number M13436 (see FIG. 4, SEQ ID NO: 5).

In particular embodiments, biomarker panel tests to predict preeclampsia can include measurement of ALCAM (also known as CD166). ALCAM is a membrane-bound member of the immunoglobulin superfamily and is involved in T cell activation. ALCAM can mediate cell-cell interactions through heterotypic interaction, by binding to CD6, or through homotypic interaction (binding to ALCAM expressed on other cells). An exemplary sequence for ALCAM (UniProt ID Q13740) is GenBank accession number AY644765 (see FIG. 5, SEQ ID NO: 6).

In particular embodiments, biomarker panel tests to predict preeclampsia can include measurement of FCN2 (also known as P35). Ficolins are secreted pattern recognition receptors, which are a component of the innate immune system that recognize molecular patterns associated with pathogens or cellular damage. Ficolin-2 binds to sugars present on the surface of bacteria and induces the complement pathway of the innate immune system, which can inhibit bacterial infection by inducing damage to the bacterial cell membrane. An exemplary sequence for FCN2 (UniProt ID Q15485) is GenBank accession number D49353 (see FIG. 6, SEQ ID NO: 7).

MMP-7, gpIIbIIIa, Siglec-6, Activin A, ALCAM, and/or FCN2 are "biomarkers" or "markers" in the context of the present disclosure. Biomarkers include the protein forms of the markers as well as associated nucleic acids, oligonucleotides, and metabolites, together with their related metabolites, mutations, isoforms, variants, polymorphisms, modifications, fragments, subunits, degradation products, elements, and other analytes or sample-derived measures. Biomarkers can also include mutated proteins, mutated nucleic acids, variations in copy numbers, and/or transcript variants. Biomarkers also encompass combinations of any one or more of the foregoing measurements, including temporal trends and differences. Particular embodiments of biomarkers include MMP-7 (SEQ ID NO: 1); gpIIbIIIa (SEQ ID NOs: 2-3); Siglec-6 (SEQ ID NO: 4); Activin A (SEQ ID NO: 5); ALCAM (SEQ ID NO: 6); and/or FCN2 (SEQ ID NO: 7).

Protein expression patterns can be evaluated using any method that provides a quantitative measure and is suitable for evaluation of multiple markers extracted from samples. Exemplary methods include: ELISA sandwich assays, mass spectrometric detection, calorimetric assays, binding to a protein array (e.g., antibody array), or fluorescent activated cell sorting (FACS). Approaches can use labeled affinity reagents (e.g., antibodies, small molecules, etc.) that recognize epitopes of one or more protein products in an ELISA, antibody array, or FACS screen.

In particular embodiments, the preeclampsia markers can be measured using immunoassay techniques. Immunoassays are laboratory procedures that utilize antibodies and/or antigens to detect a molecule. In particular embodiments, an immunoassay can be quantitative by using secondary antibodies that are coupled to a fluorescent, chemiluminescent, or colorimetric probe.

In particular embodiments, the preeclampsia markers can be detected using antibody-based techniques. In particular embodiments, MMP-7 can be detected using an anti-MMP-7 antibody. An example of a commercially available anti-MMP-7 antibody is anti-MMP-7 ab5706, available from Abcam. In particular embodiments, gpIIbIIIa can be detected using an anti-gpIIbIIIa antibody. An example of a commercially available anti-gpIIbIIIa antibody is anti-gpIIbIIIa ab662, available from Abcam. In particular embodiments, Siglec-6 can be detected using an anti-Siglec-6 antibody. An example of a commercially available anti-Siglec-6 antibody is anti-Siglec-6 antibody ab38581, available from Abcam. In particular embodiments, Activin A can be detected using an anti-Activin A antibody. An example of a commercially available anti-Activin A antibody is mouse anti-Activin A ab89387, available from Abcam. In particular embodiments, ALCAM can be detected using an anti-ALCAM antibody. An example of a commercially available anti-ALCAM antibody is anti-ALCAM ab109215, available from Abcam. In particular embodiments, FCN2 can be detected using an anti-FCN2 antibody. An example of a commercially available anti-FCN2 antibody is anti-103145, available from Abcam.

In particular embodiments, the preeclampsia markers can be measured using an aptamer based assay. Aptamers are small oligonucleotides or peptides that can bind to specific ligands. Aptamers can be used in an array wherein each spot or well of the array can be coated with a specific aptamer to bind to a specific protein.

Protein detection can include detection of full-length proteins, protein fragments, mature proteins, pre-proteins, polypeptides, isoforms, mutations, variants, post-translationally modified proteins, and variants thereof, and can be detected in any suitable manner. Levels of biomarkers can be determined at the protein level, e.g., by measuring the serum levels of proteins. Such methods are well-known in the art and include, e.g., immunoassays based on antibodies to proteins encoded by the genes, aptamers, or molecular imprints. Any biological material can be used for the detection/quantification of the protein or its activity. Alternatively, a suitable method can be selected to determine the activity of proteins. Such assays include protease assays, kinase assays, phosphatase assays, and reductase assays, among many others.

Variants of the sequences disclosed and referenced herein are also included. Variants of peptides can include those having one or more conservative amino acid substitutions. As used herein, a "conservative substitution" involves a substitution found in one of the following conservative substitutions groups: Group 1: Alanine (Ala), Glycine (Gly), Serine (Ser), Threonine (Thr); Group 2: Aspartic acid (Asp), Glutamic acid (Glu); Group 3: Asparagine (Asn), Glutamine (Gln); Group 4: Arginine (Arg), Lysine (Lys), Histidine (His); Group 5: Isoleucine (Ile), Leucine (Leu), Methionine (Met), Valine (Val); and Group 6: Phenylalanine (Phe), Tyrosine (Tyr), Tryptophan (Trp).

Additionally, amino acids can be grouped into conservative substitution groups by similar function or chemical structure or composition (e.g., acidic, basic, aliphatic, aromatic, sulfur-containing). For example, an aliphatic grouping may include, for purposes of substitution, Gly, Ala, Val, Leu, and Ile. Other groups containing amino acids that are considered conservative substitutions for one another include: sulfur-containing: Met and Cysteine (Cys); acidic: Asp, Glu, Asn, and Gln; small aliphatic, nonpolar or slightly polar residues: Ala, Ser, Thr, Pro, and Gly; polar, negatively charged residues and their amides: Asp, Asn, Glu, and Gln; polar, positively charged residues: His, Arg, and Lys; large aliphatic, nonpolar residues: Met, Leu, Ile, Val, and Cys; and large aromatic residues: Phe, Tyr, and Trp. Additional information is found in Creighton (1984) Proteins, W.H. Freeman and Company.

Variants of the protein and nucleic acid sequences disclosed or referenced herein also include sequences with at least 70% sequence identity, 80% sequence identity, 85% sequence, 90% sequence identity, 95% sequence identity, 96% sequence identity, 97% sequence identity, 98% sequence identity, or 99% sequence identity to the protein and nucleic acid sequences disclosed or referenced herein and particularly including SEQ ID NOs:1-7.

"% sequence identity" or "% identity" refers to a relationship between two or more sequences, as determined by comparing the sequences. In the art, "identity" also means the degree of sequence relatedness between proteins or nucleic acid sequences as determined by the match between strings of such sequences. "Identity" (often referred to as "similarity") can be readily calculated by known methods, including those described in: Computational Molecular Biology (Lesk, A. M., ed.) Oxford University Press, NY (1988); Biocomputing: Informatics and Genome Projects (Smith, D. W., ed.) Academic Press, NY (1994); Computer Analysis of Sequence Data, Part I (Griffin, A. M., and Griffin, H. G., eds.) Humana Press, NJ (1994); Sequence Analysis in Molecular Biology (Von Heijne, G., ed.) Academic Press (1987); and Sequence Analysis Primer (Gribskov, M. and Devereux, J., eds.) Oxford University Press, NY (1992). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR, Inc., Madison, Wis.). Multiple alignment of the sequences can also be performed using the Clustal method of alignment (Higgins and Sharp CABIOS, 5, 151-153 (1989)) with default parameters (GAP PENALTY=10, GAP LENGTH PENALTY=10). Relevant programs also include the GCG suite of programs (Wisconsin Package Version 9.0, Genetics Computer Group (GCG), Madison, Wis.); BLASTP, BLASTN, BLASTX (Altschul, et al., J. Mol. Biol. 215:403-410 (1990)); DNASTAR (DNASTAR, Inc., Madison, Wis.); and the FASTA program incorporating the Smith-Waterman algorithm (Pearson, Comput. Methods Genome Res., [Proc. Int. Symp.] (1994), Meeting Date 1992, 111-20. Editor(s): Suhai, Sandor. Publisher: Plenum, New York, N.Y.). Within the context of this disclosure it will be understood that where sequence analysis software is used for analysis, the results of the analysis are based on the "default values" of the program referenced. As used herein "default values" will mean any set of values or parameters which originally load with the software when first initialized.

Using sequence information provided by public database entries for the biomarkers described herein, expression of the biomarker can be detected and measured using techniques well-known to those of skill in the art. For example, nucleic acid sequences in the sequence databases that correspond to nucleic acids of biomarkers can be used to construct primers and probes for detecting and/or measuring biomarker nucleic acids. These probes can be used in, e.g., Northern or Southern blot hybridization analyses, ribonuclease protection assays, and/or methods that quantitatively amplify specific nucleic acid sequences. As another example, sequences from sequence databases can be used to construct primers for specifically amplifying biomarker sequences in, e.g., amplification-based detection and quantitation methods such as reverse-transcription based polymerase chain reaction (RT-PCR) and PCR. When alterations in gene expression are associated with gene amplification, nucleotide deletions, polymorphisms, post-translational modifications and/or mutations, sequence comparisons in test and reference populations can be made by comparing relative amounts of the examined DNA sequences in the test and reference populations.

A number of methods for obtaining expression data can be used singly or in combination for determining expression patterns and profiles in the context of the present disclosure. For example, DNA and RNA expression patterns can be evaluated by northern analysis, PCR, RT-PCR, quantitative real-time RT-PCR analysis with TaqMan assays, FRET detection, monitoring one or more molecular beacon, hybridization to an oligonucleotide array, hybridization to a cDNA array, hybridization to a polynucleotide array, hybridization to a liquid microarray, hybridization to a microelectric array, molecular beacons, cDNA sequencing, clone hybridization, cDNA fragment fingerprinting, serial analysis of gene expression (SAGE), subtractive hybridization, differential display and/or differential screening.

Gene expression changes can be related to epigenetic variations (e.g. DNA methylation). Epigenetic regulation mechanisms do not involve a change to the DNA sequence. Instead, epigenetic variations include covalent modification of DNA, RNA, and the proteins associated with DNA. These in turn can result in changes to the conformation of DNA and accessibility of regulators to the DNA. Such changes cannot be identified simply by gene sequencing. Janssen, et al., Particle and Fibre Toxicology, 10:22 (2013) studied methylation in placental tissue using methods published by Tabish, et al., PLoS ONE 2012, 7:e34674 and by Godderis, et al., Epigenomics 4:269-277 (2012). MS-MLPA (Methylation-specific Multiplex ligation-dependent probe amplification) can be used to study methylation status of specific genes, for example in Proctor, et al., Clin. Chem. 52:1276-1283 (2006). Materials and methods for MS-MLPA as used in published studies can be obtained from MRC-Holland, Amsterdam, The Netherlands. Additional methods are reviewed and compared in Shen, et al., Curr. Opin. Clin. Nutr. Metab. Care. 10:576-81 (2007); Gu et al., Nature Methods 7:133-138 (2010); Bock et al., Nature Biotech. 28:1106-1114 (2010); and Harris et al., Nature Biotech. 28:1097-1105 (2010).

In particular embodiments, the kits and methods to predict preeclampsia include use of an array to measure markers. A variety of solid phase arrays can also be employed to determine expression patterns. Exemplary formats include membrane or filter arrays (e.g., nitrocellulose, nylon), pin arrays, and bead arrays (e.g., in a liquid "slurry"). Essentially any solid support capable of withstanding the reagents and conditions necessary for performing the particular expression assay can be utilized. For example, functionalized glass, silicon, silicon dioxide, modified silicon, any of a variety of polymers, such as (poly)tetrafluoroethylene, (poly)vinylidenedifluoride, polystyrene, polycarbonate, or combinations thereof can all serve as the substrate for a solid phase array.

In particular embodiments, arrays can include "chips" composed, e.g., of one of the above-specified materials. Polynucleotide probes, e.g., RNA or DNA, such as cDNA, synthetic oligonucleotides, and the like, or protein-binding ligands such as antibodies, peptides, aptamers, antigen-binding fragments or derivatives thereof, that specifically interact with expression products of individual components of the candidate library are affixed to the chip in a logically ordered manner, i.e., in an array. In addition, any molecule with a specific affinity for either the sense or anti-sense sequence of the marker nucleotide sequence (depending on the design of the sample labeling), can be fixed to the array surface without loss of specific affinity for the marker and can be obtained and produced for array production, for example, proteins that specifically recognize the specific nucleic acid sequence of the marker, ribozymes, peptide nucleic acids (PNA), or other chemicals or molecules with specific affinity.

Detailed discussion of methods for linking nucleic acids and proteins to a chip substrate, are found in, e.g., U.S. Pat. Nos. 5,143,854; 6,087,112; 5,215,882; 5,707,807; 5,807,522; 5,958,342; 5,994,076; 6,004,755; 6,048,695; 6,060,240; 6,090,556; and 6,040,138.

Microarray expression may be detected by scanning the microarray with a variety of laser or CCD-based scanners, and extracting features with software packages, for example, Imagene (Biodiscovery, Hawthorne, Calif.), Feature Extraction Software (Agilent), Scanalyze (Eisen, M. 1999. SCANALYZE User Manual; Stanford Univ., Stanford, Calif. Ver 2.32), or GenePix (Axon Instruments).

"Measuring" includes determining, assessing, calculating, and/or analyzing a value or set of values associated with a sample by measurement of marker (i.e., analyte) levels in the sample. "Determining" may further include comparing levels against constituent levels in a sample or set of samples from the same subject or other subject(s). The MMP-7, gpIIbIIIa, Siglec-6, Activin A, ALCAM, FCN2 and/or other biomarkers of the present disclosure can be determined by any of various conventional methods known in the art.

In particular embodiments, quantitative data obtained for the markers of interest and other dataset components can be subjected to an analytic process with chosen parameters. The parameters of the analytic process may be those disclosed herein or those derived using the guidelines described herein. The analytic process used to generate a result may be any type of process capable of providing a result useful for classifying a sample, for example, comparison of the obtained dataset with a reference dataset, a linear algorithm, a quadratic algorithm, a decision tree algorithm, or a voting algorithm. The analytic process may set a threshold for determining the probability that a sample belongs to a given class (high risk of preeclampsia or low risk of preeclampsia). The probability preferably is at least 50%, or at least 60%, or at least 70%, or at least 80%, or at least 90% or higher.

A "dataset" as used herein is a set of numerical values resulting from evaluation of a sample (or population of samples) under a desired condition. The values of the dataset can be obtained, for example, by experimentally obtaining measures from a sample and constructing a dataset from these measurements; or alternatively, by obtaining a dataset from a service provider such as a laboratory, or from a database or a server on which the dataset has been stored.

In particular embodiments, a dataset of values is determined by measuring biomarkers from a non-pregnant subject or a pregnant subject who does not have or did not subsequently develop preeclampsia. Datasets can be used by an interpretation function to derive a preeclampsia score, which can provide a quantitative measure of likelihood that a subject will develop preeclampsia.

The sensitivity of a diagnostic measure is also referred to as the true positive rate, or the recall in some fields. It denotes the proportion of positive results (development of preeclampsia) that are correctly identified as such. The specificity of a diagnostic measure is also referred to as the true negative rate. It denotes the proportion of negatives that are correctly identified as such (no development of preeclampsia).

In particular embodiments, the kits and methods disclosed herein have at least a 60% sensitivity and a 90% specificity. In particular embodiments, the kits and methods disclosed herein have at least an 85% sensitivity and a 90% specificity. In particular embodiments, the kits and methods disclosed herein preeclampsia is identified with a sensitivity of 60% or greater, 65% or greater, 70% or greater, 75% or greater, 80% or greater, 85% or greater.

A used herein, the term "change of abundance" with regard to changes in the marker levels can refer to an increase or decrease of more than 20%, more than 30%, more than 40%, more than 50%, more than 60%, more than 70%, more than 80%, more than 90%, more than 100%, more than 150%, or more than 200% compared to a reference level. In particular embodiments, "change of abundance" measures can be evaluated independently against a reference level without consideration of earlier comparisons in the same subject. In particular embodiments, "change of abundance" can refer to any statistically significant increase or decrease in a measure as compared to a control or reference population.

As used herein, "unchanged" measures are evaluated in relation to a previous comparison in the same subject and denote a failure to achieve a statistically significant change in a score towards or away from a reference level in the particular subject.

In particular embodiments, the amount of the biomarker(s) can be measured in a sample and used to derive a preeclampsia risk score, which preeclampsia risk score is then compared to a "reference level". Reference levels can include "normal", "control", or "no preeclampsia" levels or values, defined according to, e.g., discrimination limits or risk defining thresholds, in order to define cut-off points and/or abnormal values for preeclampsia. The reference level then is the level of one or more biomarkers or combined biomarker indices typically found in a subject who did not develop preeclampsia over the course of pregnancy. Other terms for "reference levels" include "index," "baseline," "standard", etc. Such normal levels can vary, based on whether a biomarker is used alone or in a formula combined with other biomarkers to output a score. Alternatively, the reference level can be a database of biomarker patterns from previously tested subjects who did not develop preeclampsia over a clinically relevant time period, such as over the course of a pregnancy.

In particular embodiments, "reference level" can refer to a standardized value for the markers which represents a level not associated with preeclampsia. The reference level can be a universal reference level which is useful across a variety of testing locations or can be a reference level specific for the testing location and specific immunoassay used to measure the preeclampsia markers. In particular embodiments, the reference levels of the preeclampsia markers and/or reference weighted score is derived from (i) an individual; (ii) a group of individuals; (iii) a subject before pregnancy; or (iv) a pregnant subject who did not develop preeclampsia over the course of their pregnancy; wherein the samples are obtained from individuals who did not develop preeclampsia. In particular embodiments, the subject whose samples are used to obtain a reference level can be different from the subject who is being tested for risk of onset of preeclampsia. In particular embodiments, the subject whose samples are used to obtain a reference level can be the same subject who is being tested for risk of onset of preeclampsia. When the reference level is based on samples collected from the same subject, reference level samples can be collected at earlier time-points, either before pregnancy or at earlier time-points during pregnancy.

In particular embodiments, measurement of preeclampsia markers can be used in a model to calculate a preeclampsia risk score. In particular embodiments, the preeclampsia risk score is calculated using a linear discriminant analysis (LDA) model. LDA is a method that can be used to classify data points into decision zones based on a linear combination of features. In particular embodiments, the decision zones can include high risk of preeclampsia onset and low risk of preeclampsia onset. In particular embodiments, LDA can use a linear combination of data from the measurements of preeclampsia markers to distinguish between decision zones. In particular embodiments, LDA can be used to calculate preeclampsia risk score (1), wherein one or more samples are taken from a subject between the 16th and 22nd week of pregnancy and the measurement of early-onset preeclampsia markers can be used as input values in the model. In particular embodiments, LDA can be used to calculate preeclampsia risk score (2), wherein one or more samples are taken from a subject between the 22nd and 28th week of pregnancy and the measurement of early-onset preeclampsia markers can be used as input values in the model. In particular embodiments, LDA can be used to calculate preeclampsia risk score (3), wherein one or more samples are taken from a subject between the 28th and 32nd week of pregnancy and the measurement of early-onset preeclampsia markers can be used as input values in the model. In particular embodiments, LDA can be used to calculate preeclampsia risk score (4), wherein one or more samples are taken from a subject between the 16th and 22nd week of pregnancy and the measurement of late-onset preeclampsia markers can be used as input values in the model. In particular embodiments, LDA can be used to calculate preeclampsia risk score (5), wherein one or more samples are taken from a subject between the 22nd and 28th week of pregnancy and the measurement of early-onset, MVU associated preeclampsia markers can be used as input values in the model. In particular embodiments, a preeclampsia score is an output value of the LDA. In particular embodiments, a preeclampsia score can be a numerical value, wherein a score above a particular threshold value indicates high risk of onset of preeclampsia and a score below a particular threshold value indicates low risk of onset of preeclampsia. In particular embodiments, an output value can be associated with positive risk, which can mean that the patient is at high risk (e.g., higher than average) of developing clinical symptoms of preeclampsia. In particular embodiments, an output score can be associated with negative risk (e.g., average or lower than average), which can mean that the patient is at low risk of developing clinical symptoms of preeclampsia.

"Interpretation functions," as used herein, can mean the transformation of a set of observed data into a meaningful determination of particular interest; e.g., an interpretation function may be a predictive model that is created by utilizing one or more statistical algorithms to transform a dataset of observed biomarker data into a meaningful determination of likelihood of preeclampsia in a subject.

"Predict" or "prediction" as used herein can mean the identification of patients who are at increased risk of developing the clinical symptoms of preeclampsia, and who are more likely than not to develop the clinical symptoms of preeclampsia if therapeutic interventions are not initiated. As indicated elsewhere, the clinical symptoms of preeclampsia include: systolic or diastolic blood pressures of ≥140 and/or ≥90 mmHg, respectively, at two or more time points, between 4 hours (h) and 1 week apart; proteinuria of ≥300 mg protein in a 24 h urine sample, or two random urine specimens obtained between 4 h and 1 week apart containing ≥1+ protein on a dipstick; and maternal vascular underperfusion (MVU).

Systems disclosed herein include kits to assay the biomarkers disclosed herein. Also disclosed herein are kits including one or more binding domains (e.g., antibodies, binding proteins, primers, aptamers, and/or probes that bind to the biomarkers described herein). In particular embodiments, kits disclosed herein include detection reagents, detectable labels or subsets thereof, and/or other reagents that can be used to detect the preeclampsia biomarkers. A safety notice can be associated with such reagents.

In particular embodiments, the kits may include instructions for using the kit in the methods disclosed herein. In particular embodiments, the kit may include instructions regarding preparation of the antibodies, binding proteins, primers and/or probes, use of the antibodies, binding proteins, primers and/or probes, proper disposal of the related waste, interpretation of results, and the like. The instructions can be in the form of printed instructions provided inside a carton containing the kit. The instructions can also be printed on the carton and/or on other portions of the kit. Instructions may be in the form of a sheet, pamphlet, brochure, CD-Rom, or computer-readable device, or can provide directions to instructions at a remote location, such as a website. The instructions may be in English and/or in any national or regional language.

In particular embodiments, the kits described herein include some or all of the necessary supplies needed to use the kit, thereby eliminating the need to locate and gather such supplies. The supplies can include pipettes, pipette tips, buffers, reagents, plates, films, tubes, thermocyclers, tube racks, gloves, sterilizing liquids, and the like.

In particular embodiments, the kits described herein include instructions for interpretation of preeclampsia risk scores and direction as to how to proceed with therapeutic interventions. In particular embodiments, a positive prediction result directs a therapeutic intervention so that the clinical development of preeclampsia is avoided, reduced, or delayed. Therapeutic interventions can include antiplatelet drugs; antihypertensive drugs; dietary supplementation with antioxidants (primarily vitamins C and E) and at least 1 g of calcium a day; rest; and exercise.

The Examples below are included to demonstrate particular embodiments of the disclosure. Those of ordinary skill in the art should recognize in light of the present disclosure that many changes can be made to the specific embodiments disclosed herein and still obtain a like or similar result without departing from the spirit and scope of the disclosure.

Example 1

Objectives: 1) To identify maternal plasma proteins predictive of late preeclampsia; and 2) to determine whether stratification of patients with late preeclampsia according to placental histopathology improves the prediction performance.

Materials and methods: Proteomics technique: The SOMAmer® (Slow Off-rate Modified Aptamers, SomaLogic Inc, Boulder, Colo.) binding reagents that allow the measurement of over 1,125 proteins in maternal plasma samples were used (Gold et al., PloS one 2010; 5(12): e15004; Davies et al., PNAS 2012; 109(49):19971-6; and SomaLogic. SOMAmer® Technical Notes. Proteomics profiling was performed by Somalogic Inc who commercializes the technology and all needed reagents. The patient serum sample was diluted and then incubated with the respective SOMAmer® mixes pre-immobilized onto streptavidin (SA)-coated beads. The beads were washed to remove all non-specifically associated proteins and other matrix constituents. Proteins that remained specifically bound to their cognate SOMAmer® reagents were tagged using an NHS-biotin reagent. After the labeling reaction, the beads were exposed to an anionic competitor solution that prevents non-specific interactions from reforming after they are disrupted. Essentially pure cognate-SOMAmer® complexes and unbound (free) SOMAmer® reagents are released from the SA beads using ultraviolet light that cleaves the photo-cleavable linker. The photo-cleavage eluate, which contains all SOMAmer® reagents (some bound to a biotin-labeled protein and some free), was separated from the beads and then incubated with a second streptavidin-coated bead that binds the biotin-labeled proteins and the biotin-labeled protein-SOMAmer® complexes. The free SOMAmer® reagents were then removed during subsequent washing steps. In the final elution step, protein-bound SOMAmer® reagents were released from their cognate proteins using denaturing conditions. These SOMAmer® reagents were then quantified by hybridization to custom DNA microarrays. The Cyanine-3 signal from the SOMAmer® reagent was detected on microarrays.

A case-control longitudinal study was conducted to include 90 patients with normal pregnancies (controls) and 76 patients with late preeclampsia (cases; delivery 234 weeks of gestation). Maternal plasma samples were collected throughout gestation [median number of samples per patient (interquartile range, IQR) controls: 2(2-5); cases: 5(4.8-6)]. The abundance of 1,125 proteins was measured using an Aptamer based proteomics technique.

Protein abundance in normal pregnancies was modeled using linear mixed effects models to estimate mean and standard deviation (SD) as a function of gestational age. Data for all samples was then expressed as Z-scores relative to the mean (log) value in normal pregnancies. Multi-marker prediction models were built using data from one of four gestational age intervals (8-16, 16.1-22, 22.1-28, 28.1-32 weeks of gestation). Receiver operating characteristic (ROC) curves were compared for top biomarkers between cases of late preeclampsia with and without maternal vascular underperfusion (MVU) lesion in the placenta.

Figure 7B:
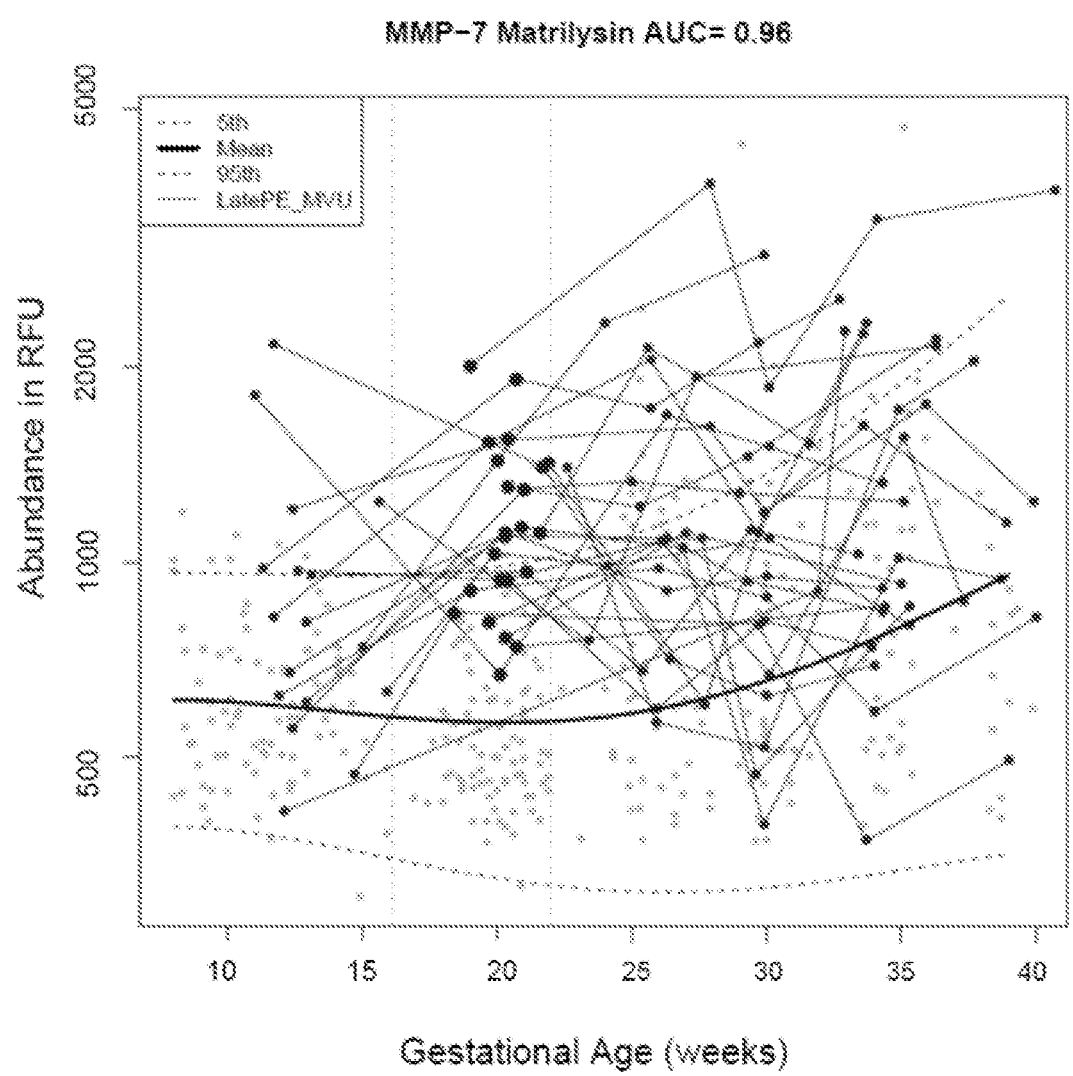
Figure 7C:
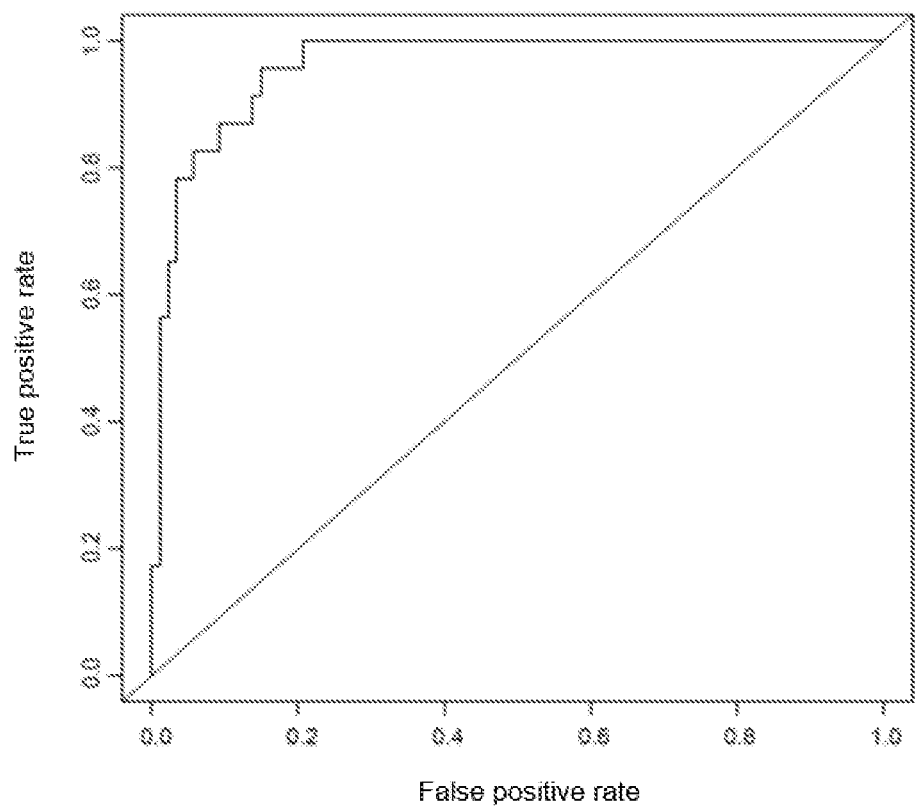

Results: 1) The highest sensitivity for predicting late preeclampsia prior to diagnosis was achieved by a Biomarker-1 (MMP-7) between 16.1-22 weeks of gestation [area under the curve (AUC)=0.83 FIG. 7A, sensitivity of 62%, at 10% false positive rate (FPR)]; 2) the mean level of this marker was higher in cases than in controls only in early (<22 weeks), but not in late gestation; and 3) disaggregation of patients based on the presence of MVU lesions in the placenta improves the predictive ability (FIG. 7B) for preeclampsia (late preeclampsia with MVU: AUC=0.96 (FIG. 7C, sensitivity=87% at 10% FPR; and late preeclampsia without MVU: AUC=0.76, sensitivity=50% at 10% FPR; p<0.0001).

Conclusions: This study reports the discovery of a novel biomarker for the prediction of late preeclampsia, which can be used between 16-22 weeks of gestation. This biomarker has a unique behavior, as differences are observed only in early but not in late gestation. Moreover, that classification of preeclampsia according to histopathologic findings improves the prediction of disease was demonstrated. This has implications for the identification of targets for intervention.

Example 2

Objective: To identify maternal plasma proteins predictive of early preeclampsia before the onset of disease.

Materials and methods: A discovery case-control longitudinal study was designed to include 90 patients with normal pregnancies (controls) and 34 patients with early preeclampsia (cases; delivery<34 weeks of gestation). Maternal plasma samples were collected throughout gestation [median number of samples per patient (interquartile range, IQR) controls: 2(2-5); cases: 4(3-4)]. The abundance of 1,125 proteins was measured in each sample using Aptamer proteomics based multiplex assays. A validation independent study was performed in a different experimental batch including 50 patients with normal pregnancies sampled longitudinally [median 4, IQR (4-4)] and 40 cases sampled once at the time of diagnosis.

Multi-marker prediction models were built using data from one of four gestational age intervals (8-16, 16.1-22, 22.1-28, and 28.1-32 weeks of gestation), and performance was estimated using 50 bootstrap trials. In each trial, a training set of women (both cases and controls) was selected with replacement to build a disease prediction model, and performance was estimated based on data from women not included in the training set (testing set). The testing set performance was averaged over all bootstrap trials, and a final model was also trained and tested on all data to compute an apparent performance.

Figure 8A:
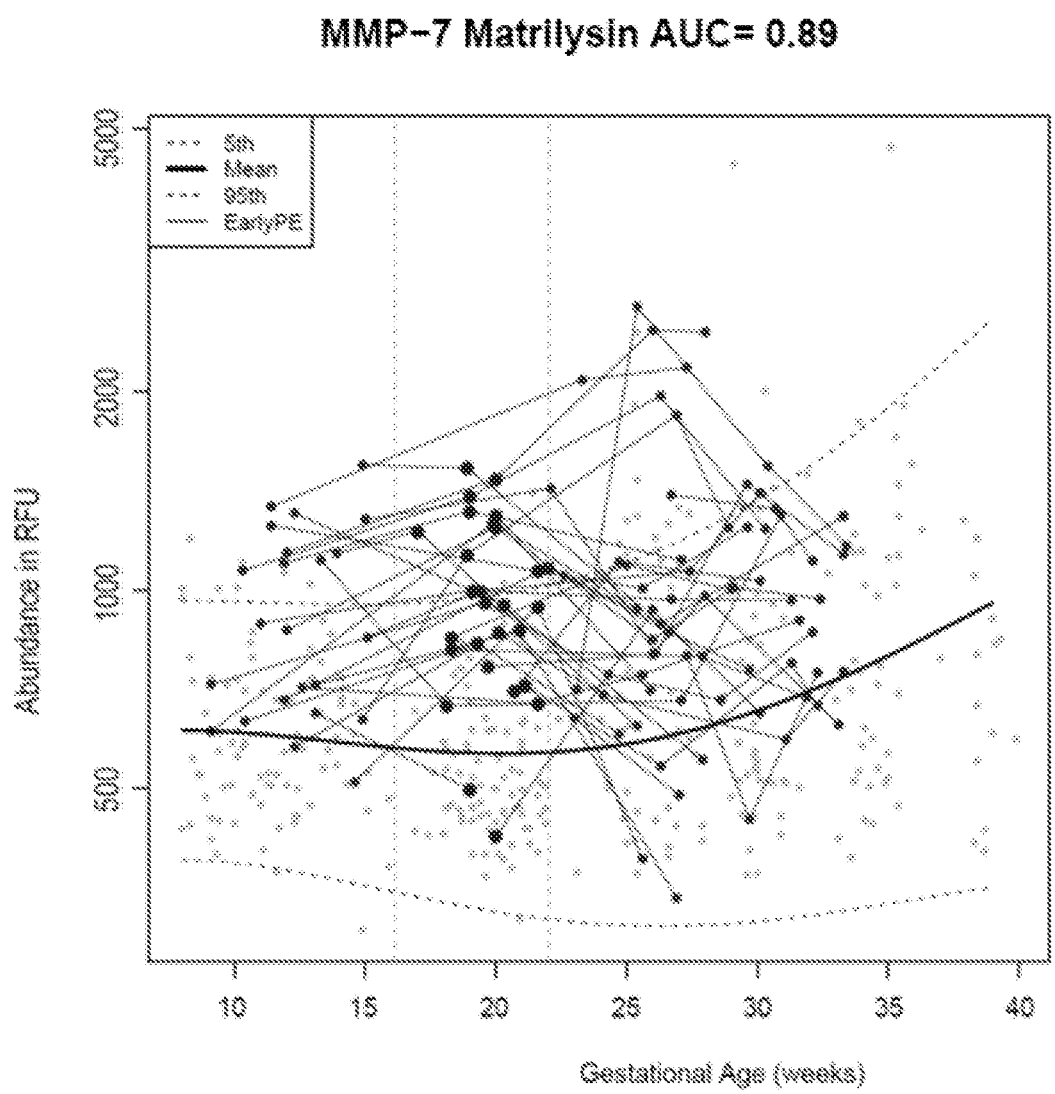
FIGS. 8A-8C. Longitudinal profiles of maternal plasma MMP-7 (FIG. 8A) and gpIIbIIIa (FIG. 8B) in patients with early preeclampsia (PE) (gray dots). In the gestational age interval 16.1-22 weeks, the discrimination between early PE (dark gray dots) and controls (light gray dots) was best for these two markers. Receiver operating characteristic (ROC) curves for MMP-7 and gpIIbIIIa (FIG. 8C).
Figure 8B:
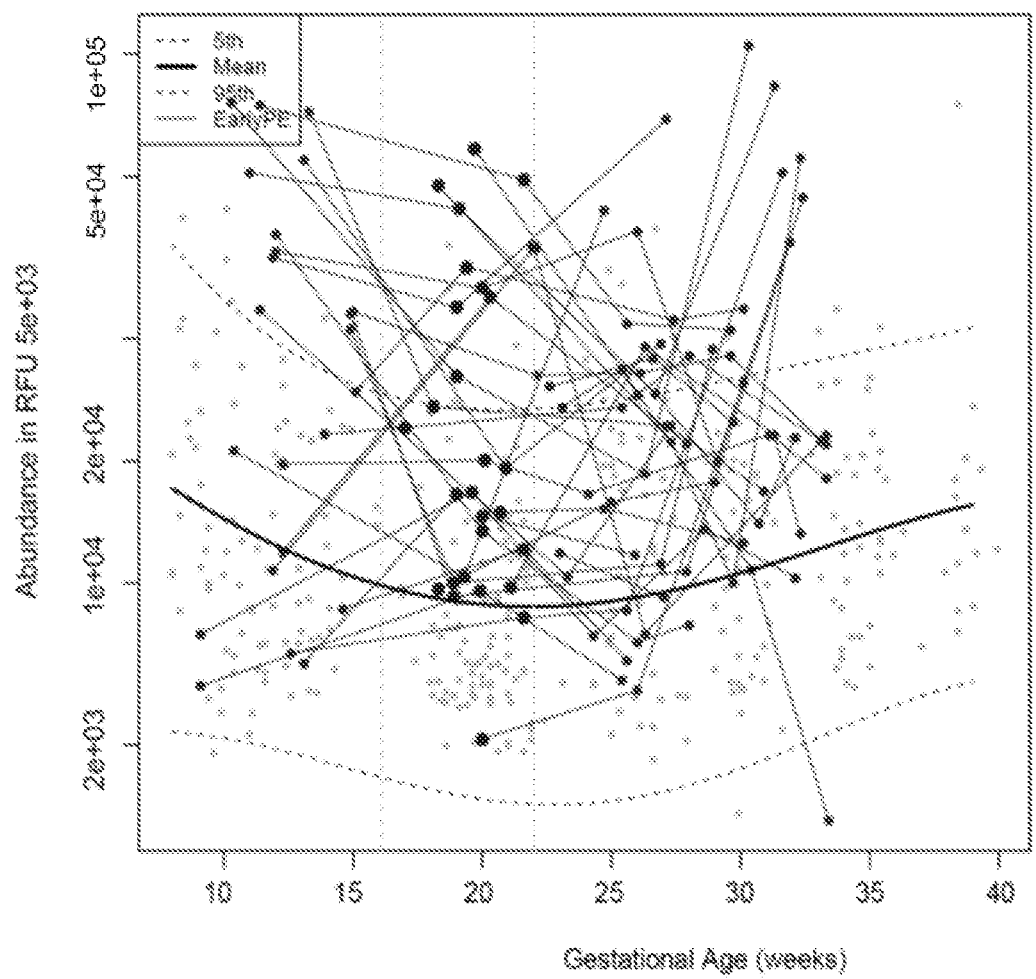
Figure 8C:
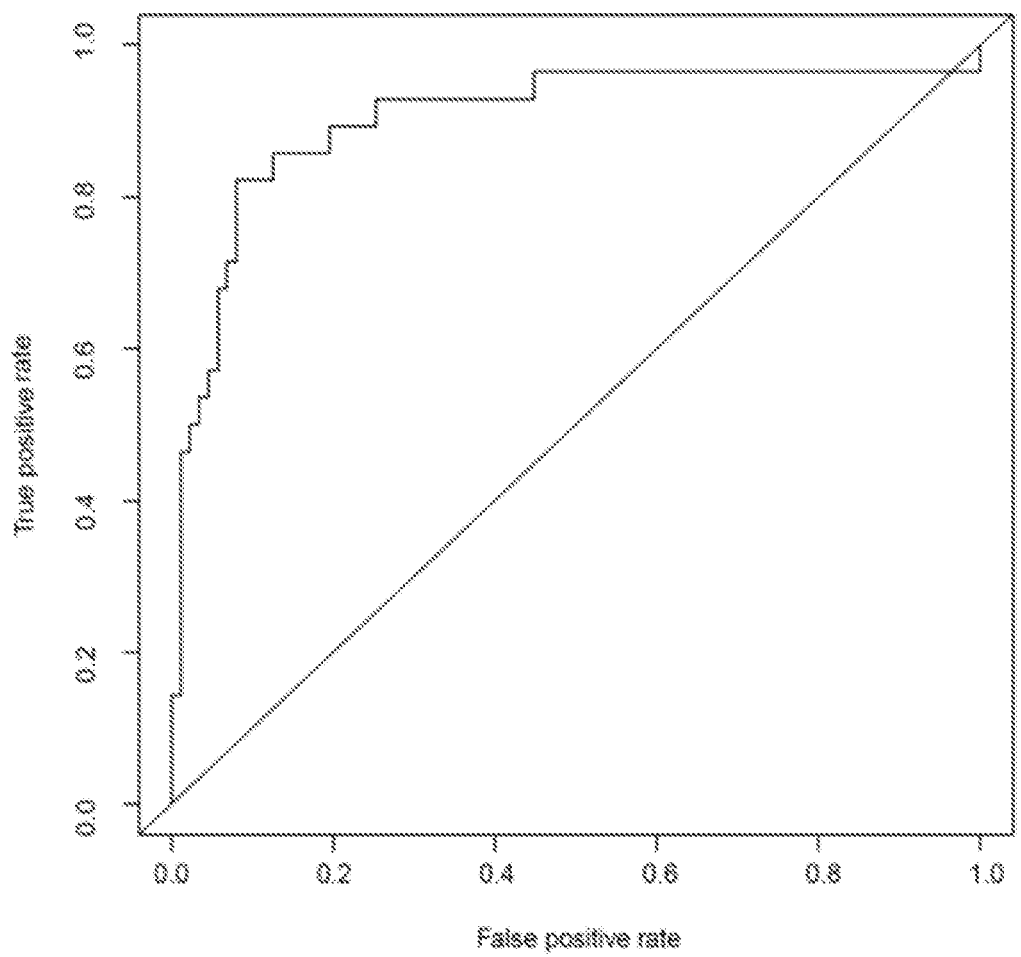

Results: 1) At 16.1-22 weeks of gestation, a combination of MMP-7 (FIG. 8A) and gpIIbIIIa (FIG. 8B) predicts the subsequent development of early preeclampsia with AUC=0.9 (FIG. 8C) and bootstrap sensitivity of 72% (82% apparent sensitivity) at 90% specificity; 2) these 2 biomarkers were selected in the best marker combination in 90% and 17% of the bootstrap trials, respectively; 3) interestingly, both proteins showed increased abundance in cases compared to controls early in pregnancy (<22 weeks) but neither later in gestation based on the discovery set (FIGS. 8A-8B) nor at the time of disease (validation set).

Figure 9A:
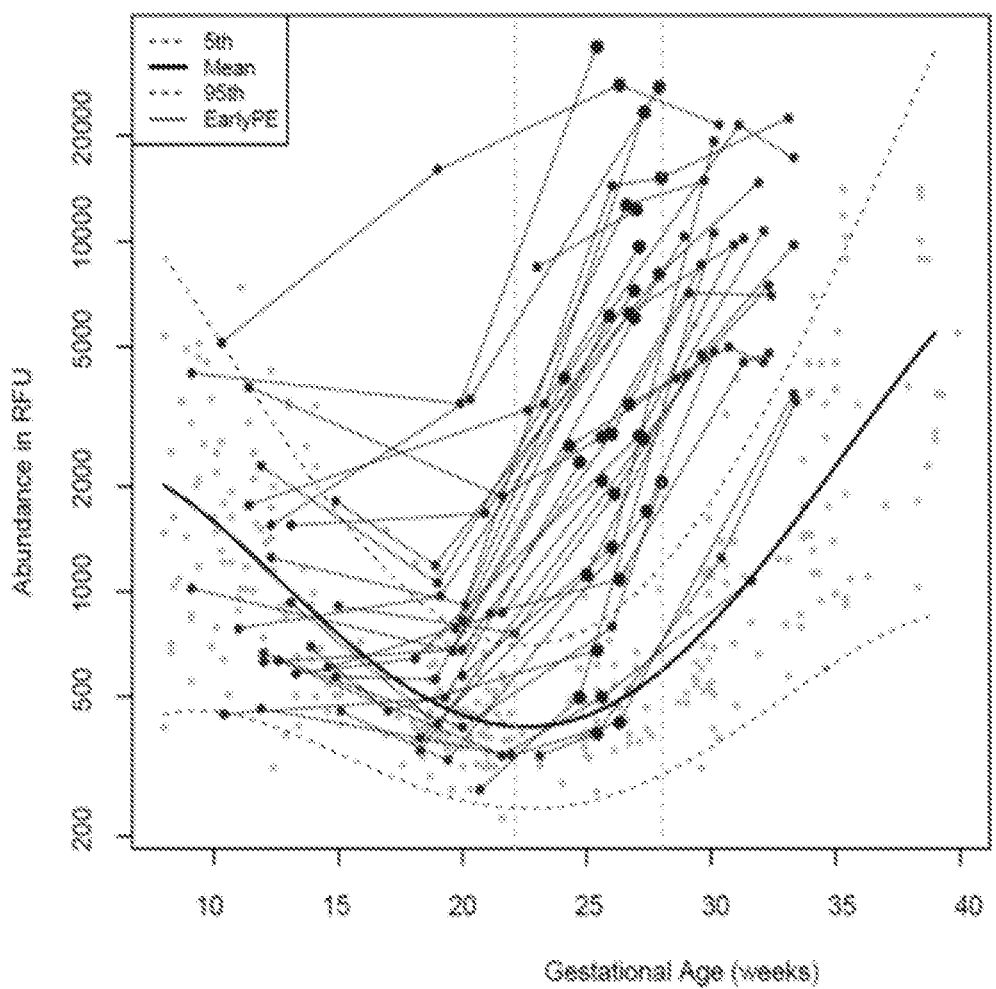
FIGS. 9A-9C. Longitudinal profiles of maternal plasma Siglec-6 (FIG. 9A) in patients with early preeclampsia (PE). Longitudinal profiles of a maternal plasma Activin A (FIG. 9B) in patients with early preeclampsia (PE). Longitudinal profiles of a maternal plasma Siglec-6 (FIG. 9C) in patients with early PE MVU. The best interval for the discrimination between early PE MVU and controls was observed in the interval 22-28 weeks of gestation.
Figure 9B:
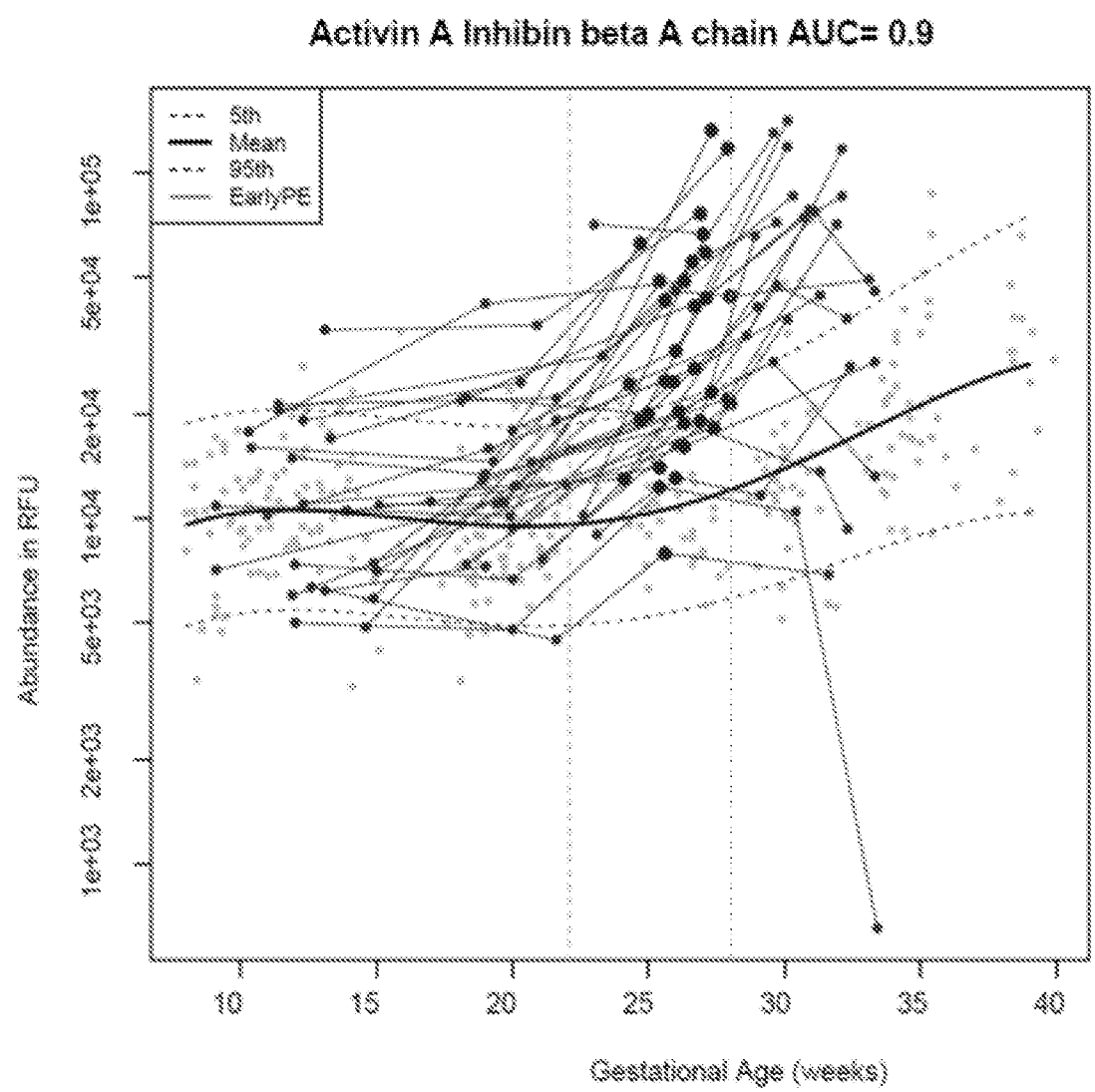
Figure 9C:
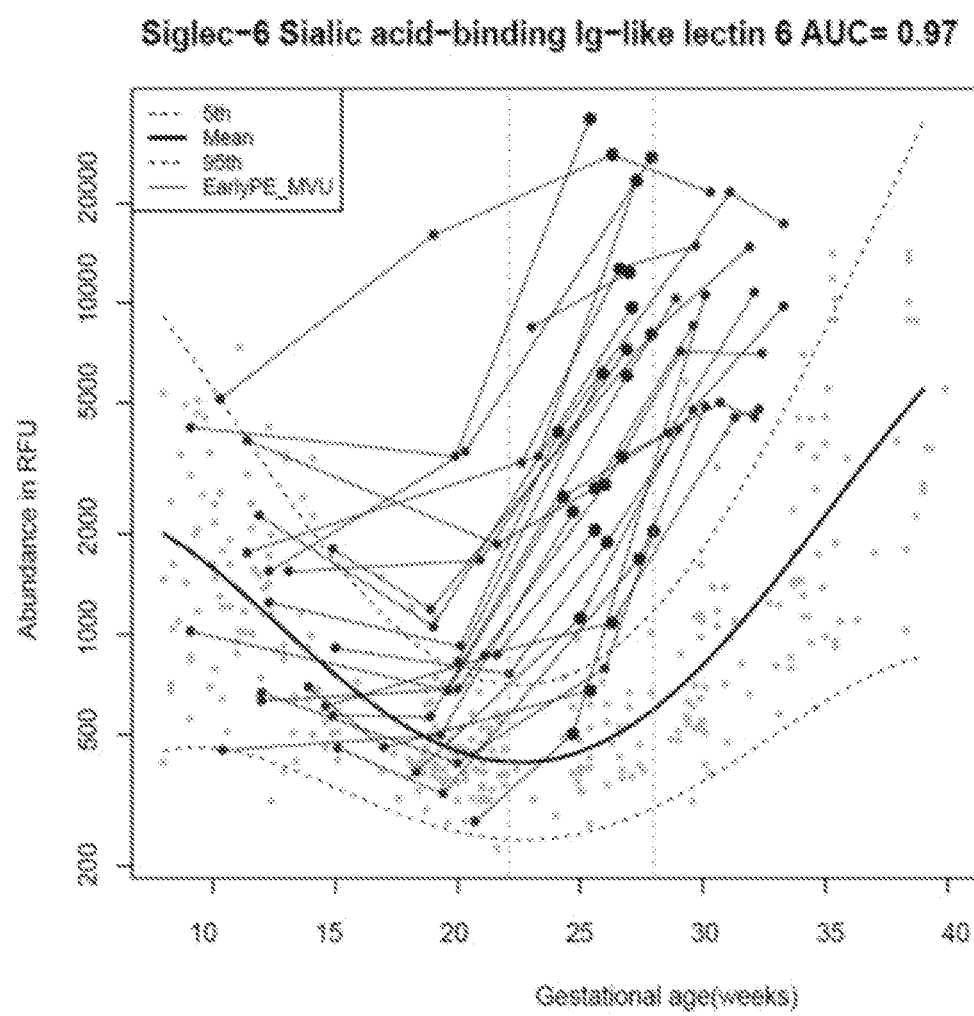

At 22-28 weeks of gestation Siglec-6 (FIG. 9A) and Activin A (FIG. 9B) predicted the subsequent development of early preeclampsia. The AUC for Siglec-6 is 0.91 and the AUC for Activin A is 0.9. Additionally, disaggregation of patients based on the presence of MVU lesions in the placenta improves the predictive ability for preeclampsia by Siglec-6 (AUC=0.97, FIG. 9C).

Figure 10A:
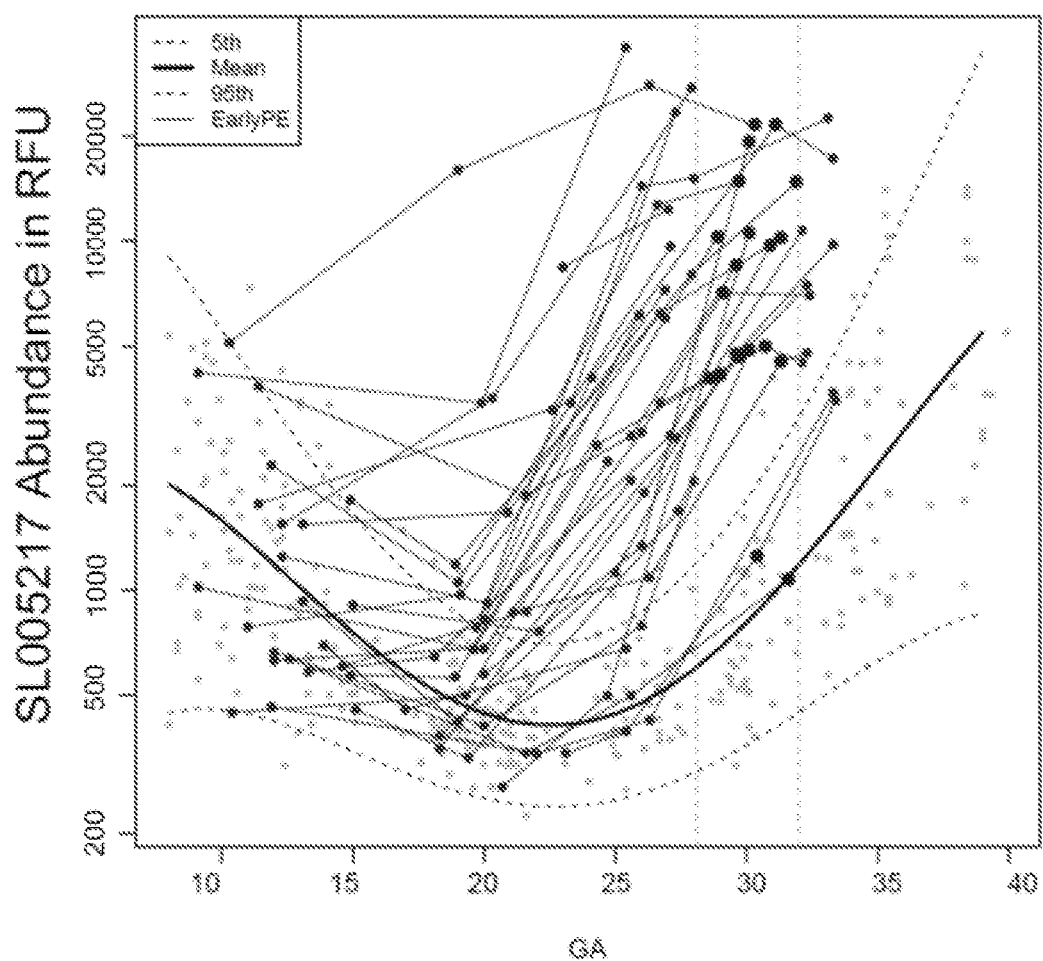
FIGS. 10A-10C. Longitudinal profiles of maternal plasma Siglec-6 (FIG. 10A) in patients with early preeclampsia (PE). Longitudinal profiles of a maternal plasma ALCAM (FIG. 10B) in patients with early preeclampsia (PE). Longitudinal profiles of a maternal plasma FCN2 (FIG. 10C) in patients with early preeclampsia (PE).
Figure 10B:
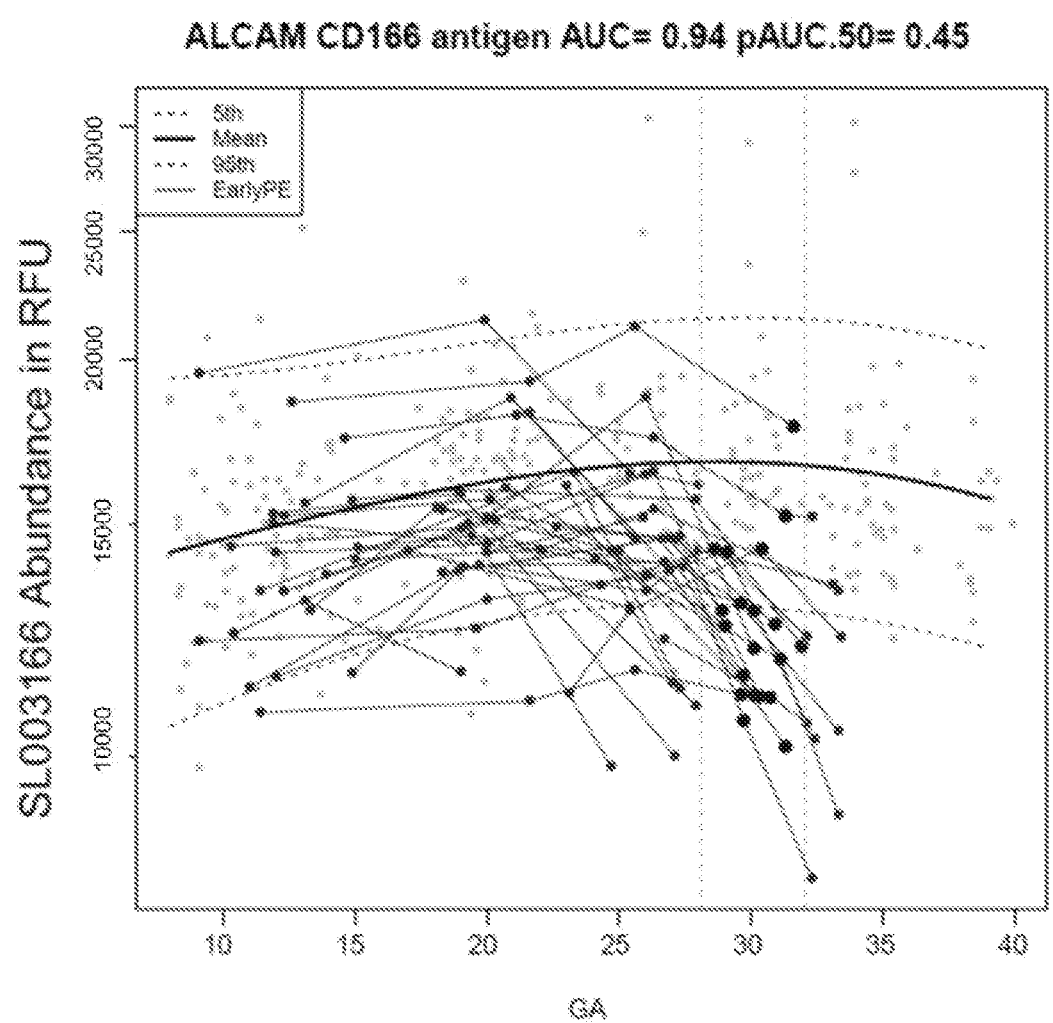
Figure 10C:
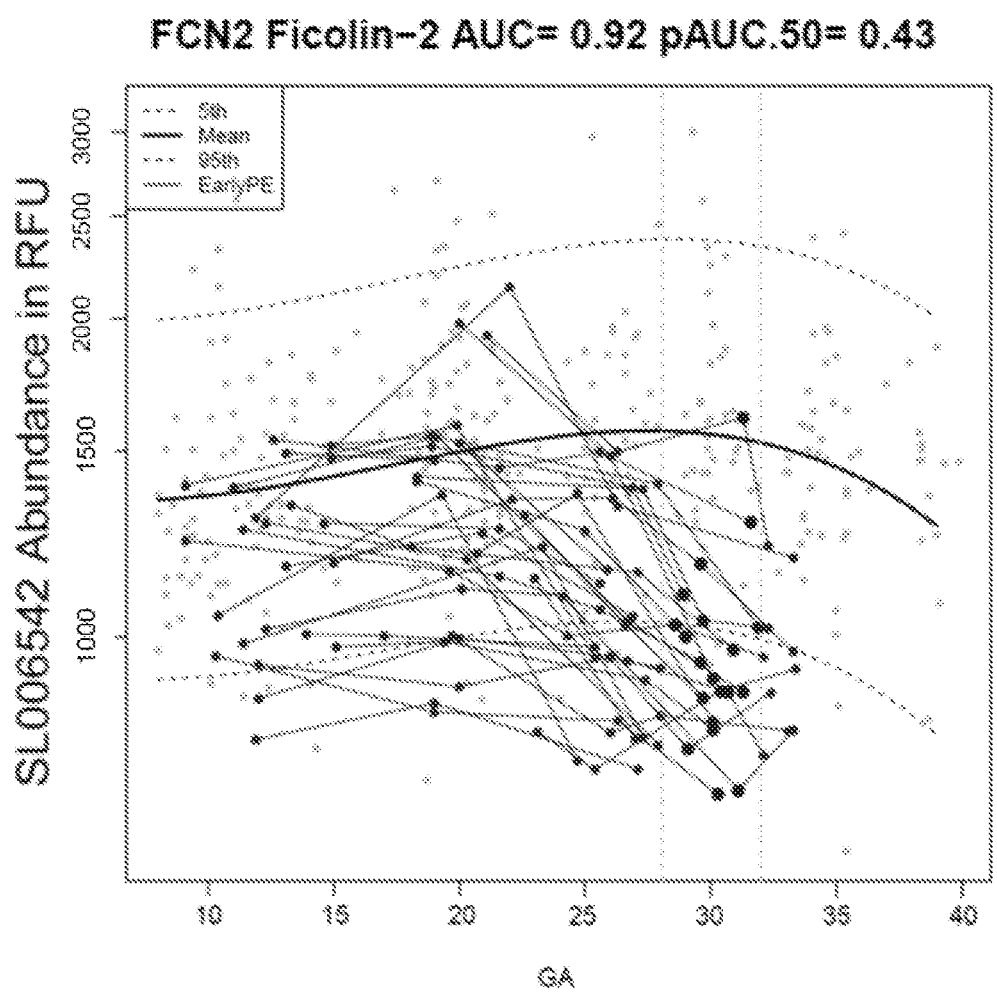

At 28-32 weeks of gestation, a combination of Siglec-6, ALCAM, and FCN2 predicts the development of early preeclampsia. The AUC for Siglec-6 in this time range is 0.93 (FIG. 10A), the AUC for ALCAM in this time range is 0.94 (FIG. 10B), and the AUC for FCN2 in this time range is 0.92 (FIG. 10C).

Conclusions: Novel biomarkers which can predict the subsequent development of early preeclampsia from 16 weeks of gestation are described. In particular, MMP-7 has a unique profile as differences in its abundance are observed in early, but not in late gestation. This is of value in the identification of patients at risk since therapeutic (e.g. prophylactic) intervention is possible.

As will be understood by one of ordinary skill in the art, each embodiment disclosed herein can comprise, consist essentially of, or consist of its particular stated element, step, ingredient or component. Thus, the terms "include" or "including" should be interpreted to recite: "comprise, consist of, or consist essentially of." As used herein, the transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment. As used herein, a material effect would cause a statistically significant reduction in the specificity of the prediction of preeclampsia based on a sample obtained between 16-22 weeks gestational age.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the", and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually, or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above described elements in all possible variations thereof is encompassed by the invention unless otherwise indicated herein or otherwise clearly contradicted by context.

Specific embodiments disclosed herein may be further limited in the claims using "consisting of" or "consisting essentially of" language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A method comprising:
obtaining a plasma or serum sample derived from a pregnant human subject in the 16$^{th}$ to 22$^{nd}$ week of gestation; and
contacting the sample with at least two binding ligands, at least one of which binds biomarker MMP-7 and at least one of which binds biomarker gpIIbIIIa.

2. A method comprising:
assaying a serum or plasma sample obtained from a pregnant human subject for expression level of:
biomarker proteins MMP-7 and gpIIbIIIa, and wherein the sample is obtained from the pregnant human subject in the 16$^{th}$ to 22$^{nd}$ week of gestation.

3. The method of claim 2 wherein:
the assaying comprises loading samples into:
one or more well coated with MMP-7 binding ligands, and
one or more wells coated with gpIIbIIIa binding ligands.

4. The method of claim 2, further comprising:
assaying a second serum or plasma sample obtained from the pregnant human subject for expression level of:
biomarker proteins Siglec-6 and Activin A, wherein the second sample is obtained from the pregnant human subject in the 22$^{nd}$ to 28$^{th}$ week of gestation; and/or
biomarker proteins Siglec-6, ALCAM, and FCN2, wherein the second sample is obtained from the pregnant human subject in the 28$^{th}$ to 32$^{nd}$ week of gestation.

5. The method of claim 4 wherein:
the second sample is obtained between the 22$^{nd}$ and 28$^{th}$ week of gestation; and
the assaying comprises loading the second sample into:
one or more wells coated with Siglec-6 binding ligands, and
one or more wells coated with Activin A binding ligands.

6. The method of claim 4 wherein:
the second sample is obtained between the 22$^{nd}$ and 32$^{nd}$ week of gestation; and
the assaying comprises loading the second sample into:
one or more wells coated with Siglec-6 binding ligands,
one or more wells coated with ALCAM binding ligands, and
one or more wells coated with FCN2 binding ligands.

7. The method of claim 1 wherein:
the contacting comprises loading samples into:
one or more well coated with MMP-7 binding ligands and
one or more wells coated with gpIIbIIIa binding ligands.

8. The method of claim 1, further comprising:
obtaining a second plasma or serum sample derived from the pregnant human subject in the 22$^{nd}$ to 28$^{th}$ week of gestation; and
contacting the second sample with binding ligands that bind a biomarker, wherein the binding ligands comprise:
at least one ligand that binds biomarker Siglec-6; and
at least one ligand that binds biomarker Activin A; and
obtaining a third plasma or serum sample derived from the pregnant human subject in the 28$^{th}$ to 32$^{nd}$ week of gestation; and
contacting the second sample with binding ligands that bind a biomarker, wherein the binding ligands comprise:
at least one ligand that binds biomarker Siglec-6; and
at least one ligand that binds biomarker ALCAM; and
at least one ligand that binds biomarker FCN2.

9. The method of claim 8 wherein:
for the second sample, the contacting comprises loading samples into:
one or more wells coated with Siglec-6 binding ligands; and
one or more wells coated with Activin A binding ligands;
and
for the third sample, the contacting comprises loading samples into:
one or more wells coated with Siglec-6 binding ligands,
one or more wells coated with ALCAM binding ligands, and
one or more wells coated with FCN2 binding ligands.

10. The method of claim 1, further comprising:
obtaining a second plasma or serum sample derived from the pregnant human subject;
and
contacting the second sample with binding ligands that bind a biomarker;
wherein
(A) the second plasma or serum sample is derived from the pregnant human subject in the 22$^{nd}$ to 28$^{th}$ week of gestation; and
the binding ligands comprise:
at least one ligand that binds biomarker Siglec-6; and
at least one ligand that binds biomarker Activin A;
or
(B) the second plasma or serum sample is derived from the pregnant human subject in the 28$^{th}$ to 32$^{nd}$ week of gestation; and
the binding ligands comprise:
at least one ligand that binds biomarker Siglec-6; and
at least one ligand that binds biomarker ALCAM; and
at least one ligand that binds biomarker FCN2.

11. The method of claim 10 wherein:
when the second sample is obtained between the 28$^{th}$ and 32$^{nd}$ week of gestation,
the contacting comprises loading the second sample into:
one or more wells coated with Siglec-6 binding ligands,
one or more wells coated with ALCAM binding ligands, and
one or more wells coated with FCN2 binding ligands.

12. The method of claim 10 wherein:
when the second sample is obtained between the 22$^{nd}$ and 28$^{th}$ week of gestation,
the contacting comprises loading the second sample into:
- one or more wells coated with Siglec-6 binding ligands and
- one or more wells coated with Activin A binding ligands.

* * * * *